(12) United States Patent  (10) Patent No.: US 8,292,808 B2
Miller et al.  (45) Date of Patent: Oct. 23, 2012

(54) IMPLANTABLE SENSOR METHOD AND SYSTEM

(75) Inventors: Michael E. Miller, Culver City, CA (US); Rajiv Shah, Rancho Palos Verdes, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 1013 days.

(21) Appl. No.: 12/211,783

(22) Filed: Sep. 16, 2008

(65) Prior Publication Data

US 2009/0030297 A1  Jan. 29, 2009

Related U.S. Application Data

(62) Division of application No. 10/334,686, filed on Dec. 31, 2002, now Pat. No. 7,736,309.

(60) Provisional application No. 60/414,290, filed on Sep. 27, 2002.

(51) Int. Cl.
    A61B 5/00 (2006.01)
    A61B 5/05 (2006.01)
    A61M 31/00 (2006.01)

(52) U.S. Cl. ........ 600/309; 600/345; 600/347; 600/365; 604/48; 604/65; 604/66; 604/67

(58) Field of Classification Search .................. 600/347, 600/365
    See application file for complete search history.

(56) References Cited

U.S. PATENT DOCUMENTS

| | | | |
|---|---|---|---|
| 3,731,681 A | 5/1973 | Blackshear et al. | |
| 3,923,060 A | 12/1975 | Ellinwood, Jr. | |
| 4,003,379 A | 1/1977 | Ellinwood, Jr. | |
| 4,240,438 A | 12/1980 | Updike et al. | |
| 4,479,796 A | 10/1984 | Kallok | |
| 4,484,987 A | 11/1984 | Gough | |
| 4,568,335 A | 2/1986 | Updike et al. | |
| 4,596,575 A | 6/1986 | Rosenberg et al. | |
| 4,628,928 A | 12/1986 | Lowell | |
| 4,650,547 A | 3/1987 | Gough | |

(Continued)

FOREIGN PATENT DOCUMENTS

JP    02-071724 A    3/1990

(Continued)

OTHER PUBLICATIONS

Office Action dated Aug. 31, 2010 from related Japanese application No. 2004-540104.

(Continued)

*Primary Examiner* — Patricia Mallari

(57) ABSTRACT

Systems and methods for non-vascular sensor implantation and for measuring physiological parameters in areas of a body where the physiological parameters are heterogeneous. An implant unit is implanted in an area of a body and a foreign body capsule is allowed to form around the implant unit area. A sensor may be directed into a body cavity such as, for example, the peritoneal space, subcutaneous tissues, the foreign body capsule, or other area. A subcutaneous area of the body may be tunneled for sensor placement. Spatially separated sensing elements may be used for detecting individual amounts of the physiological parameter. An overall amount of the physiological parameter may be determined by calculating a statistical measurement of the individual sensed amounts in the area. Another embodiment of the invention, a multi-analyte measuring device, may include a substrate having an electrode array on one side and an integrated circuit on another side.

20 Claims, 21 Drawing Sheets

U.S. PATENT DOCUMENTS

| | | | |
|---|---|---|---|
| 4,703,756 A | 11/1987 | Gough et al. | |
| 4,721,677 A | 1/1988 | Clark, Jr. | |
| 4,734,184 A | 3/1988 | Burleigh et al. | |
| 4,757,022 A | 7/1988 | Shults et al. | |
| 4,771,772 A | 9/1988 | DeWitt | |
| 4,802,479 A | 2/1989 | Haber et al. | |
| 4,874,500 A | 10/1989 | Madou et al. | |
| 4,890,620 A | 1/1990 | Gough | |
| 4,911,168 A | 3/1990 | Davis | |
| 4,994,167 A | 2/1991 | Shults et al. | |
| 5,039,390 A | 8/1991 | Hampp et al. | |
| 5,094,951 A | 3/1992 | Rosenberg | |
| 5,139,485 A | 8/1992 | Smith et al. | |
| 5,266,688 A | 11/1993 | Rosenberg | |
| 5,300,106 A | 4/1994 | Dahl et al. | |
| 5,317,269 A | 5/1994 | Mills et al. | |
| 5,322,063 A | 6/1994 | Allen et al. | |
| 5,324,518 A | 6/1994 | Orth et al. | |
| 5,328,460 A | 7/1994 | Lord et al. | |
| 5,357,969 A | 10/1994 | Herleikson | |
| 5,411,647 A | 5/1995 | Johnson et al. | |
| 5,497,772 A | 3/1996 | Schulman et al. | |
| 5,509,410 A | 4/1996 | Hill et al. | |
| 5,534,025 A | 7/1996 | Moussy | |
| 5,569,186 A | 10/1996 | Lord et al. | |
| 5,587,352 A | 12/1996 | Tamura et al. | |
| 5,593,852 A | 1/1997 | Heller et al. | |
| 5,660,163 A * | 8/1997 | Schulman et al. | 600/345 |
| 5,667,983 A | 9/1997 | Abel et al. | |
| 5,682,884 A | 11/1997 | Hill et al. | |
| 5,685,856 A | 11/1997 | Lehrer | |
| 5,691,932 A | 11/1997 | Reiner et al. | |
| 5,694,932 A | 12/1997 | Michel | |
| 5,696,314 A | 12/1997 | McCaffrey et al. | |
| 5,701,895 A | 12/1997 | Prutchi et al. | |
| 5,707,502 A | 1/1998 | McCaffrey et al. | |
| 5,711,868 A | 1/1998 | Maley et al. | |
| 5,728,281 A | 3/1998 | Holmstrom et al. | |
| 5,741,211 A | 4/1998 | Renirie et al. | |
| 5,741,319 A | 4/1998 | Woloszko et al. | |
| 5,770,028 A | 6/1998 | Maley et al. | |
| 5,773,270 A | 6/1998 | D'Orazio et al. | |
| 5,791,344 A | 8/1998 | Schulman et al. | |
| 5,804,048 A | 9/1998 | Wong et al. | |
| 5,919,216 A | 7/1999 | Houben et al. | |
| 5,932,175 A | 8/1999 | Knute et al. | |
| 5,941,906 A | 8/1999 | Barreras, Sr. et al. | |
| 5,965,380 A | 10/1999 | Heller et al. | |
| 5,985,129 A | 11/1999 | Gough et al. | |
| 5,987,352 A | 11/1999 | Klein et al. | |
| 5,992,211 A | 11/1999 | Skrtic | |
| 5,999,848 A | 12/1999 | Gord et al. | |
| 6,001,067 A | 12/1999 | Shults et al. | |
| 6,002,954 A | 12/1999 | Van Antwerp et al. | |
| 6,027,479 A | 2/2000 | Alei et al. | |
| 6,049,727 A | 4/2000 | Crothall | |
| D424,696 S | 5/2000 | Ray et al. | |
| D426,638 S | 6/2000 | Ray et al. | |
| 6,075,610 A | 6/2000 | Ueda et al. | |
| 6,093,167 A | 7/2000 | Houben et al. | |
| 6,103,033 A | 8/2000 | Say et al. | |
| 6,120,676 A | 9/2000 | Heller et al. | |
| 6,122,536 A | 9/2000 | Sun et al. | |
| 6,125,290 A | 9/2000 | Miesel | |
| 6,125,291 A | 9/2000 | Miesel et al. | |
| 6,134,459 A | 10/2000 | Roberts et al. | |
| 6,135,978 A | 10/2000 | Houben et al. | |
| 6,144,866 A | 11/2000 | Miesel et al. | |
| 6,159,240 A | 12/2000 | Sparer et al. | |
| 6,162,611 A | 12/2000 | Heller et al. | |
| 6,163,723 A | 12/2000 | Roberts et al. | |
| 6,175,752 B1 | 1/2001 | Say et al. | |
| 6,198,952 B1 | 3/2001 | Miesel | |
| 6,201,980 B1 | 3/2001 | Darrow et al. | |
| 6,206,871 B1 | 3/2001 | Zanon et al. | |
| 6,210,326 B1 | 4/2001 | Ehwald | |
| 6,233,471 B1 | 5/2001 | Berner et al. | |
| 6,248,080 B1 | 6/2001 | Miesel et al. | |
| 6,251,260 B1 | 6/2001 | Heller et al. | |
| 6,254,586 B1 * | 7/2001 | Mann et al. | 604/506 |
| 6,259,937 B1 * | 7/2001 | Schulman et al. | 600/345 |
| 6,261,280 B1 | 7/2001 | Houben et al. | |
| 6,264,611 B1 | 7/2001 | Ishikawa et al. | |
| 6,268,161 B1 | 7/2001 | Han et al. | |
| 6,331,244 B1 | 12/2001 | Lewis et al. | |
| 6,402,689 B1 | 6/2002 | Scarantino et al. | |
| 6,424,847 B1 * | 7/2002 | Mastrototaro et al. | 600/316 |
| 6,431,175 B1 | 8/2002 | Penner et al. | |
| 6,442,413 B1 | 8/2002 | Silver | |
| 6,558,321 B1 | 5/2003 | Burd et al. | |
| 6,692,520 B1 | 2/2004 | Gambale et al. | |
| 6,702,847 B2 | 3/2004 | DiCarlo | |
| 2001/0039374 A1 | 11/2001 | Schulman | |
| 2002/0055673 A1 * | 5/2002 | Van Antwerp et al. | 600/365 |
| 2002/0120186 A1 * | 8/2002 | Keimel | 600/365 |
| 2003/0050680 A1 | 3/2003 | Gibson et al. | |
| 2003/0078560 A1 | 4/2003 | Miller et al. | |

FOREIGN PATENT DOCUMENTS

| | | |
|---|---|---|
| JP | 05-504704 | 7/1993 |
| JP | 5-238960 | 9/1993 |
| JP | 06-189915 | 7/1994 |
| JP | 6-189915 A | 7/1994 |
| JP | 6-277201 | 10/1994 |
| JP | 06-339532 | 12/1994 |
| JP | 8-154903 | 6/1996 |
| JP | 08-233774 | 9/1996 |
| JP | 09-512200 | 12/1997 |
| JP | 10-026585 A | 1/1998 |
| JP | 11-004895 A | 1/1999 |
| JP | 11-501234 | 2/1999 |
| JP | 11-508792 | 8/1999 |
| JP | 2000-515778 | 11/2000 |
| JP | 2001-510382 A | 7/2001 |
| JP | 2001-516980 | 10/2001 |
| JP | 2002-513602 A | 5/2002 |
| JP | 2002-525153 T | 8/2002 |
| WO | WO-92/07525 | 5/1992 |
| WO | WO-92/10141 A1 | 6/1992 |
| WO | WO-96/25089 A1 | 8/1996 |
| WO | WO 97/01986 | 1/1997 |
| WO | WO 98/01071 | 1/1998 |
| WO | WO 98/28605 | 7/1998 |
| WO | WO-99/13574 | 3/1999 |
| WO | WO 99/48419 | 9/1999 |
| WO | WO 99/56613 | 11/1999 |
| WO | WO-00/18294 A1 | 4/2000 |
| WO | WO 00/33065 | 6/2000 |
| WO | WO 01/01851 A1 | 1/2001 |
| WO | WO-01/74251 A2 | 10/2001 |
| WO | WO-01/91846 | 12/2001 |
| WO | WO 02/50534 A1 | 6/2002 |

OTHER PUBLICATIONS

Decision of Rejection dated Dec. 9, 2008 for related Japanese patent application No. 2003-537480.

Office Action dated Nov. 9, 2010 from related European patent application No. 02 780 519.1.

Office Action dated Oct. 26, 2010 from related Japanese application No. 2003-537480.

Office Action dated Jun. 23, 2009 from related U.S. Appl. No. 10/334,686.

Office Action dated Dec. 16, 2008 from related U.S. Appl. No. 10/996,026.

Office Action dated Dec. 22, 2008 for JP Application No. 2003-537480.

Office Action dated Dec. 5, 2008 from related U.S. Appl. No. 10/334,686.

Office Action dated Dec. 8, 2009 for EP Application No. 03754703.1.

Office Action dated Jun. 23, 2006 from related U.S. Appl. No. 10/334,686.

Office Action dated Jun. 6, 2008 from related U.S. Appl. No. 10/334,686.

Office Action dated Mar. 14, 2005 from related U.S. Appl. No. 10/034,627.

Office Action dated Mar. 2, 2004 from related U.S. Appl. No. 10/034,627.
Office Action dated Mar. 24, 2009 for EP Application No. 02780519.1.
Office Action dated Mar. 8, 2007 from related U.S. Appl. No. 10/334,686.
Office Action dated Sep. 2, 2008 for JP application No. 2003-537480.
Office Action dated Sep. 6, 2007 from related U.S. Appl. No. 10/334,686.
Office Action issued from related Japanese patent application No. 2003-537480.
European Office Action dated Feb. 19, 2008, Application No. 03 754 703.1-1265.
PCT International Search Report as issued in International Application No. PCT/US03/29328, Mailing date Mar. 14, 2005.
PCT International Search Report as issued in International Application No. PCT/US02/33923, Mailing date May 8, 2003.
European Search Report as issued in European Application No. 03 754 703.1-2318 mailing date Apr. 27, 2006.
Notice of Allowance dated Apr. 28, 2010 from related U.S. Appl. No. 10/334,686.
Office Action dated Jun. 17, 2009 from related U.S. Appl. No. 10/996,026.
Office Action dated Aug. 4, 2009 from related Japanese Application 2004-540104.
English description of relevance for Office Action dated Aug. 4, 2009 for related Japanese patent application 2004-540104.
Notice of Allowance dated Sep. 11, 2009 from related U.S. Appl. No. 10/996,026.
Office Action dated Aug. 5, 2009 from related U.S. Appl. No. 11/286,471.
Subminiature Implantable Potentiostat and Modified Commercial Telemetry Device for Remote Glucose Monitoring—IEEE Transactions on Instrumentation and Measurement, vol. 48. No. 6 Dec. 1999—Richard D. Beach Senior Member IEEE, Falko V. Kuster, and Francis Moussy, Member IEEE.
Supplemental European Search Report dated Dec. 17, 2008 for related European Patent Application No. 02780519.1-1265/1438029.
Notice of Allowance dated Aug. 31, 2005 from related U.S. Appl. No. 10/034,627.
Notice of Allowance dated Feb. 1, 2010 from related U.S. Appl. No. 10/996,026.
Notice of Allowance dated Jan. 11, 2010 from related U.S. Appl. No. 11/286,471.
Office Action dated Jul. 21, 2009 from related JP patent application No. 2003-537480.
Office Action dated Aug. 22, 2006 for EP Application No. 03754703.1.

* cited by examiner

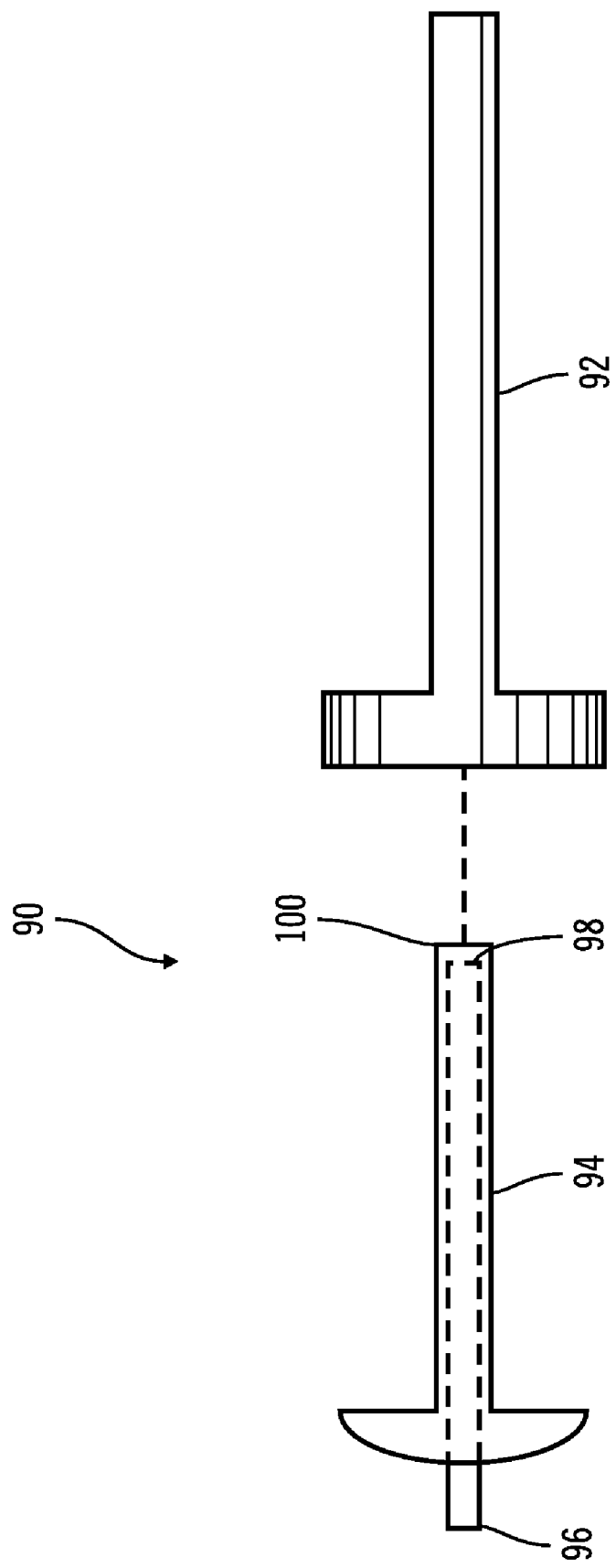

IMPLANTABLE SENSOR METHOD AND SYSTEM

CROSS-REFERENCE TO RELATED APPLICATIONS

This application is a Divisional of U.S. application Ser. No. 10/334,686, filed Dec. 31 2002 entitled "Implantable Sensor Method and System" incorporated by reference herein in its entirety, which relates to U.S. application Ser. No. 10/034,627, filed Dec. 27, 2001 and U.S. Provisional Application Ser. No. 60/335,627, filed Oct. 23, 2001, each entitled "Method and System for Non-Vascular Sensor Implantation," each of which is incorporated by reference herein in its entirety, and relates to U.S. Provisional Application, Ser. No. 60/414,290, filed Sep. 27, 2002, entitled "Implantable Sensor Method and System," which is incorporated by reference herein in its entirety and is a basis for a claim of priority.

BACKGROUND

1. Field of the Invention

The present invention relates to the field of in vivo sensors and, in particular, to in vivo sensors that are implanted in non-vascular areas of the body. The present invention also relates to a system and method for accurately measuring a physiological parameter in areas of a body (or external to the body) where amounts of the physiological parameter are heterogeneous in nature.

2. Description of Related Art

Traditional methods of physiological parameter sensing typically rely on vascular placement of a physiological parameter sensor. Such placement permits a sensing element such as, for example, a biomolecule, to make direct contact with the blood, providing sensing capabilities of blood components. Such sensing capabilities have greatly facilitated analysis, diagnosis and treatment of many debilitating diseases and medical conditions.

However, vascular placement of a physiological parameter sensor may suffer from several disadvantages. A physiological parameter sensor is not inserted into a vein without great difficulty and painstaking effort by an attending physician. Moreover, a physiological parameter sensor is not adjusted within or extracted from a vein without similar difficulty and effort.

Furthermore, vascular placement of a physiological parameter sensor subjects the sensor to a constant fluid environment. Such an environment may have several detrimental effects on the sensor. Due to constant fluidic contact, the sensor may suffer from decreased sensitivity, stability and effective life. Should a characteristic of the sensor be diminished to an extent rendering the sensor ineffective, the sensor must be removed and replaced, introducing the difficulties for both patient and physician associated with such removal and replacement. To complicate matters, every time a physiological parameter sensor is removed and replaced, it must be disconnected and reconnected to an implant unit utilizing the sensor output.

In an effort to assuage some of the disadvantages associated with vascular implantation of physiological parameter sensors, integrated sensor/implant unit systems have been developed. Such systems may be placed in or near a body cavity and may provide non-vascular sensing of physiological parameters. However, the incision required for such sensor/implant unit systems is relatively large and the trauma in the area of implantation can be significant. Such trauma generally prevents sensing of physiological parameters. Because such trauma may not subside for several weeks or a month or even longer, pre-implantation analysis methods used by the patient must continue. Without continuation of preimplantation analysis methods, a patient may go undiagnosed and untreated for many weeks, possibly even a month or longer. Such delay in treatment and diagnosis could be harmful or even fatal for patients who need daily diagnosis and treatment.

In addition, vascular implantation of physiological parameter sensors allow the sensing elements to sense a relatively homogenous amount of oxygen or other physiological parameter as it flows past the sensing elements. In contrast, when placing the sensor in a non-vascular area of the body, the physiological parameter may have a more heterogeneous nature, i.e., the amount of the physiological parameter may vary significantly at different locations within the non-vascular area. In such a case, the sensing element may sense the physiological parameter through diffusion from, for example, fluid around the sensing element. Thus, depending on the location of the sensing element within the non-vascular area, the amount of the physiological parameter sensed by the sensing element may more or less accurately represent the "overall amount" of the physiological parameter within the non-vascular area, i.e., an amount that accurately represents, for example, an average amount or other suitable statistical measure of the physiological parameter in the particular area of the body. In addition, another problem results from the fact that the heterogeneous nature of the physiological parameter being sensed by the sensing element may induce noise in the signal obtained from the sensing element.

SUMMARY OF THE DISCLOSURE

Embodiments of the present invention relate to systems and methods for non-vascular sensor implantation and to a system and method for accurately measuring a physiological parameter in areas of a body (or external to the body) where amounts of the physiological parameter are heterogeneous in nature.

A method for non-vascular implant of a sensor may include implanting an implant unit in an area of a body; allowing a foreign body capsule to form around the area of the implant unit; and directing the sensor into the foreign body capsule.

Implanting an implant unit may include incising an area of the body large enough for the implant unit. Allowing a foreign body capsule to form may comprise inserting materials around the implant unit to promote growth characteristics. A material may be placed around the implant unit for promoting growth characteristics. The implant unit may include electronics and/or a pump. The electronics may be sensor electronic or other electronics. The electronics may be integrated with the pump or may be mutually exclusive from the pump.

The sensor may be attached to the implant unit. The sensor may be attached to the implant unit prior to formation of the foreign body capsule or may be attached to the implant unit subsequent to formation of the foreign body capsule.

The method may further include incising an area of the body large enough for the sensor. The incised area of the body large enough for the sensor is smaller than an incised area of the body large enough for the implant unit.

A method for non-vascular implant of a sensor may also include incising an area of a body large enough for inserting an implant unit; incising an area remote from a sensor location for inserting a sensor; directing the sensor into a body cavity; connecting the sensor to the implant unit; and inserting the implant unit into the body. The method may further include fixing the sensor in place using suture. The implant unit may be inserted into a pocket formed when incising an area of the body large enough for inserting the implant unit.

Systems for non-vascular implant may include an implant unit for delivering drug to a human body and a sensor for detecting a physiological parameter. The sensor may be separate from and connectable to the implant unit and the sensor is placed in a non-vascular area of the human body.

The implant unit may include a pump and/or electronics. The drug delivered by the implant unit may be insulin. The sensor may include a biomolecule, a lead and a sensing element. The sensing element may be a biomolecule and the biomolecule may be a glucose oxidase enzyme. The physiological parameter sensed may be oxygen or glucose. The non-vascular area of the human body where the sensor is placed may be the peritoneum or subcutaneous tissue.

A plurality of spatially separated sensing elements may be used for detecting the physiological parameter. The sensing elements may be connectable to the implant unit. The sensing elements may be implanted in a non-vascular area of the body such that each of the sensing elements sense an individual amount of the physiological parameter within the area. The sensing elements may substantially simultaneously sense individual amounts of the physiological parameter or may sense the individual amounts in succession within a given time period. An overall amount of the physiological parameter in the area may then be determined by employing a combination of the individual sensed amounts in a statistical analysis, such as in an algorithm or combined calculation.

The plurality of spatially separated sensing elements may be a one, two, or three-dimensional array of spatially separated sensing elements. Two or more sensing elements may be spatially separated in a sensor lead by a pre-determined distance. The sensor lead may include a first sensing element located at a proximal end of the sensor lead and a second sensing element located at a distal end of the sensor lead. The sensing elements may be connected to the implant unit in a daisy chain fashion.

Each of the plurality of spatially separated sensing elements may generate a signal representing an individual sensed amount of the physiological parameter. The overall amount of the physiological parameter may be determined by calculating a statistical measurement of the individual sensed amounts represented by the generated signals. The statistical measurement may be, but is not limited to, a maximum amount for the individual sensed amounts, an average amount of the individual sensed amounts, a median of the individual sensed amounts, an arithmetic mean of the individual sensed amounts, a weighted arithmetic mean of the individual sensed amounts, or the like. In this manner, a more accurate overall measurement of the physiological parameter is possible. In addition, noise induced in the signals produced by the sensing elements may be reduced by averaging the amounts of each of the plurality of spatially separated sensing elements.

Embodiments of the present invention may also include a method for non-vascular implant of a sensor including incising an area of a body large enough for inserting an implant unit; creating a tunnel in subcutaneous tissue; directing the sensor through the tunnel; connecting the sensor to the implant unit; and inserting the implant unit into the body. The tunnel may be created using a blunt instrument such as, for example, a trocar, or other blunt instrument which minimizes trauma to the subcutaneous tissue.

Embodiments of the present invention may also include a structure for defining an in vivo implant site, the structure including a cylinder having a hollow area in an interior portion thereof, wherein a portion of the cylinder is covered with a coating. The coating may be silicone rubber and the cylinder may be a right circular cylinder. The hollow area may be sufficiently large to accept a sensor. In addition, the cylinder may have at least one hole in an outer surface thereof.

Embodiments of the present invention may also include a multi-analyte measuring device having a substrate, an electrode array on a first side of the substrate, and an integrated circuit on a second side of the substrate. The electrode array and the integrated circuit may be electrically connected. The integrated circuit processes signals or monitors signals. The electrode array may include an agent, such as, for example, an enzyme. The substrate may include channels. The multi-analyte measuring device may also include a connector for providing access to the integrated circuit. The connector may connect to a display device or a monitoring device. The multi-analyte measuring device may also include a power supply, such as, for example, a battery or a capacitor.

These and other objects, features, and advantages of embodiments of the invention will be apparent to those skilled in the art from the following detailed description of embodiments of the invention when read with the drawings and appended claims.

BRIEF DESCRIPTION OF THE DRAWINGS

FIG. 4 shows a biopsy trocar used according to an embodiment of the present invention.

DETAILED DESCRIPTION

In the following description of preferred embodiments, reference is made to the accompanying drawings which form a part hereof, and in which are shown by way of illustration specific embodiments in which the invention may be practiced. It is to be understood that other embodiments may be utilized and structural changes may be made without departing from the scope of the preferred embodiments of the present invention.

Figure 1:
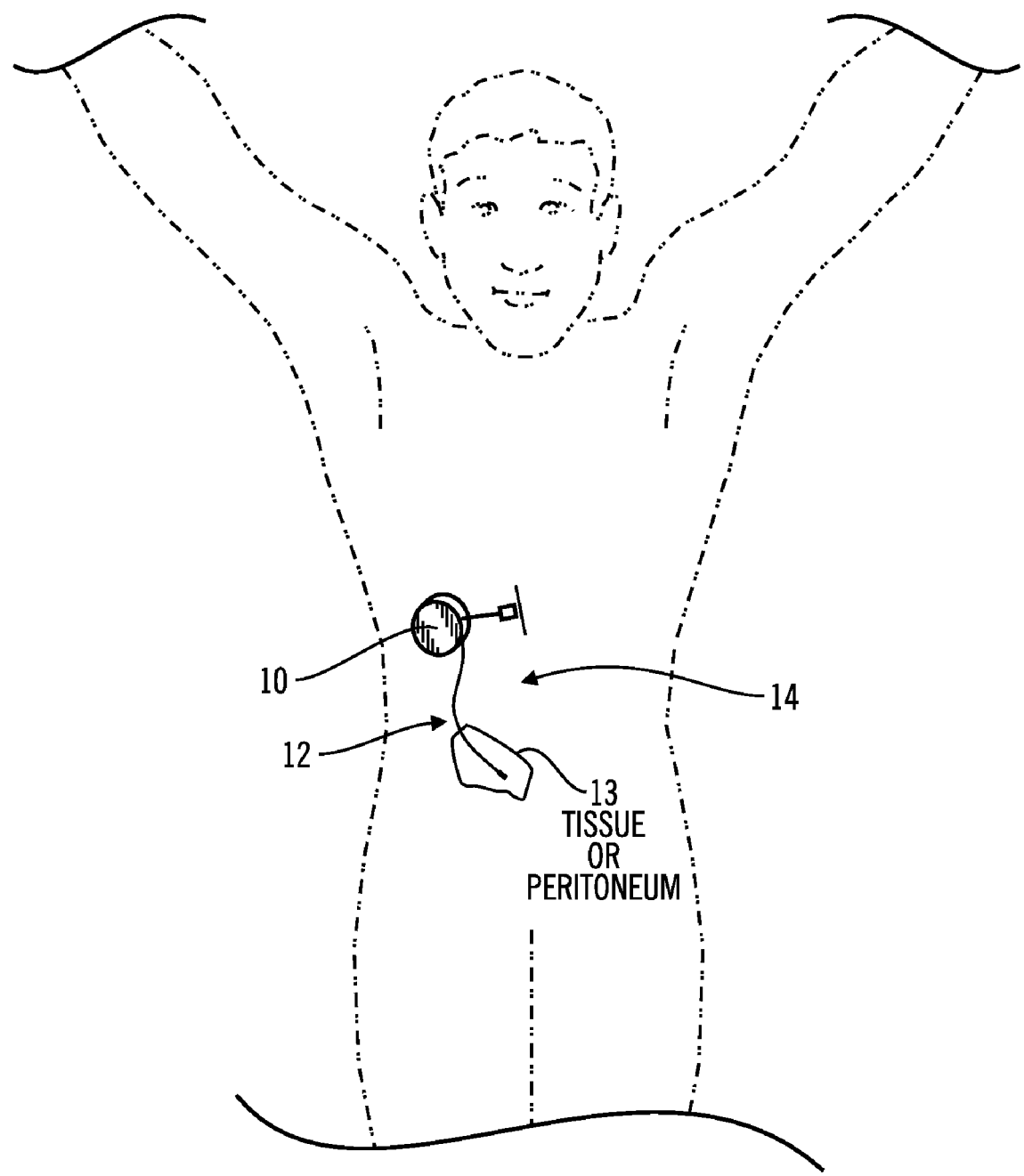
FIG. 1 shows a general position of an implant unit and a sensor in the human body according to an embodiment of the present invention.

FIG. 1 shows a general placement of an implant unit 10 and a sensor 12 in the human body according to an embodiment of the present invention. The implant unit 10 may be placed into a human body in a variety of locations such as, for example, adjacent to the abdominal cavity 14, or in other locations such as, for example, the spinal cavity or chest cavity. A sensor 12 connecting to the implant unit 10 may be located in the peritoneum 13, the membrane lining the abdominal cavity and connecting and supporting internal organs; in subcutaneous tissue 13, i.e., tissue beneath the skin; in a foreign body capsule; or in another area of the body. For example, the sensor 12 may be implanted into the shoulder area.

The implant unit 10 may contain electronics for data acquisition, data storage, data processing or other functions as may be required for physiological parameter sensing. In addition, the implant unit 10 may also contain, for example, a drug delivery system including a drug reservoir and a pumping mechanism to move a drug from the reservoir to a patient through, for example, a delivery catheter. The sensor 12 may sense a variety of physiological parameters. For example, the sensor 12 may sense glucose and oxygen and may be used in connection with the implant unit 10 to pump insulin for diabetics.

Figure 2:
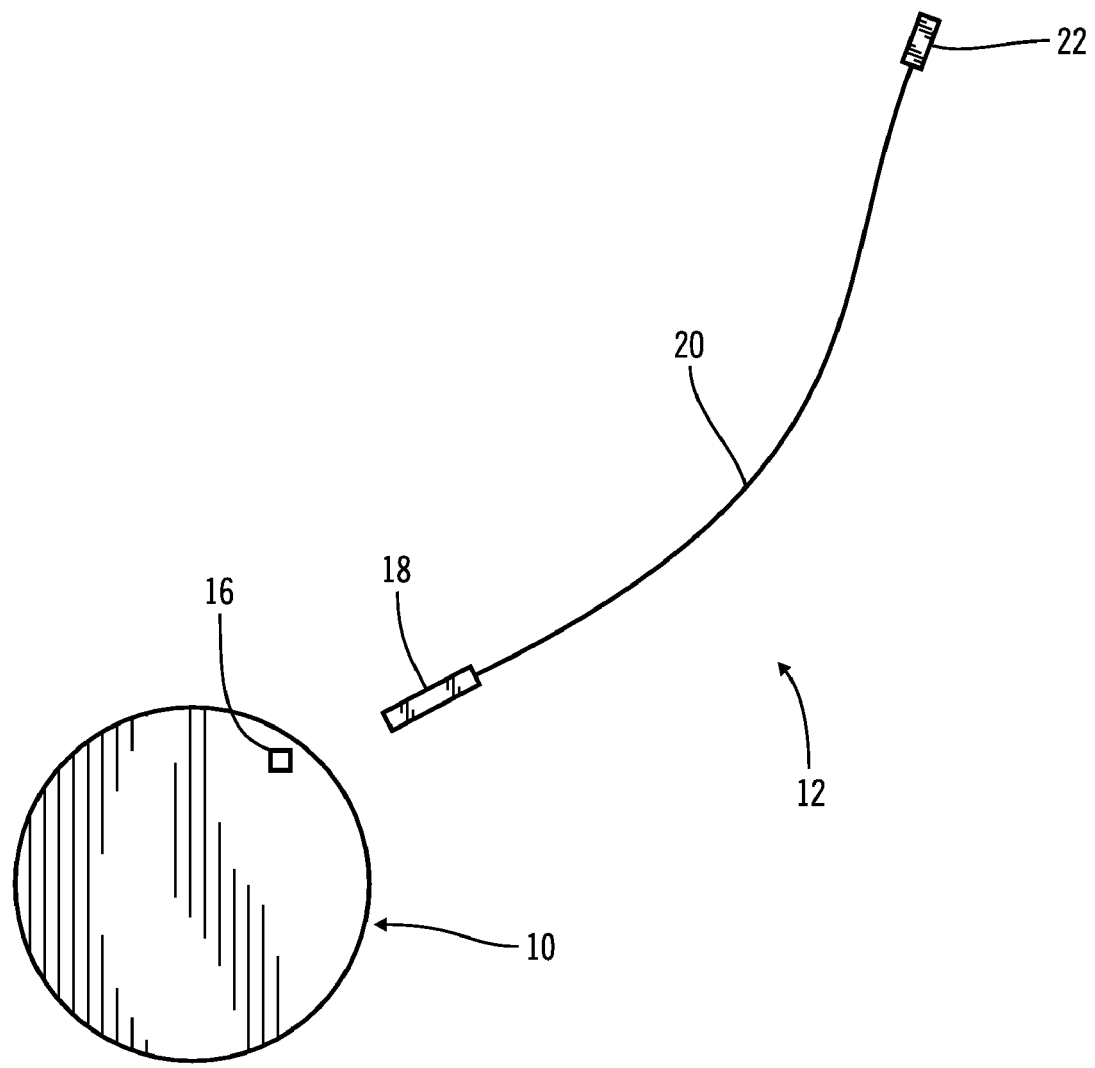
FIG. 2 shows a generalized implant unit and a sensor according to an embodiment of the present invention.

FIG. 2 shows a generalized implant unit 10 and a sensor 12 according to an embodiment of the present invention. The implant unit 10 and the sensor 12 are not integrated. They are discreet devices and may or may not be used independently of one another. The implant unit 10 and the sensor 12 may be used in conjunction with one another and may be inserted into a patient at separate times. The ability to insert the implant unit 10 and the sensor 12 into a patient at different times gives physicians and patients enhanced flexibility when implanting the devices.

As can be seen in FIG. 2, the sensor 12, according to an embodiment of the present invention, includes a connector 18, a sensor lead 20 connected to the connector at one end, and a sensing element 22 connected to the sensor lead 20 at another end. Thus, the sensing element 22 of the sensor 12 may be located away from the implant unit 10 which, as will be seen shortly, offers enhanced functionality in sensing physiological parameters.

As shown in FIG. 2, according to an embodiment of the present invention the implant unit 10 may include a receptacle 16 for accepting the connector 18 portion of the sensor 12. Also, the sensor lead 20 is not limited to any particular length. For example, the sensor lead 20 may be approximately nine inches long, permitting the sensing element 22 to be approximately nine inches from the implant unit 10. However, the sensor lead 20 may be longer or shorter than nine inches depending on the application and the particular placement of the sensing element 22 desired.

Also, the implant unit 10 may include its own lead that connects to the sensor lead 20. Thus, rather than connecting the sensor lead 20 to the receptacle 16, the sensor lead 20 may connect to an implant unit lead.

Figure 3A:
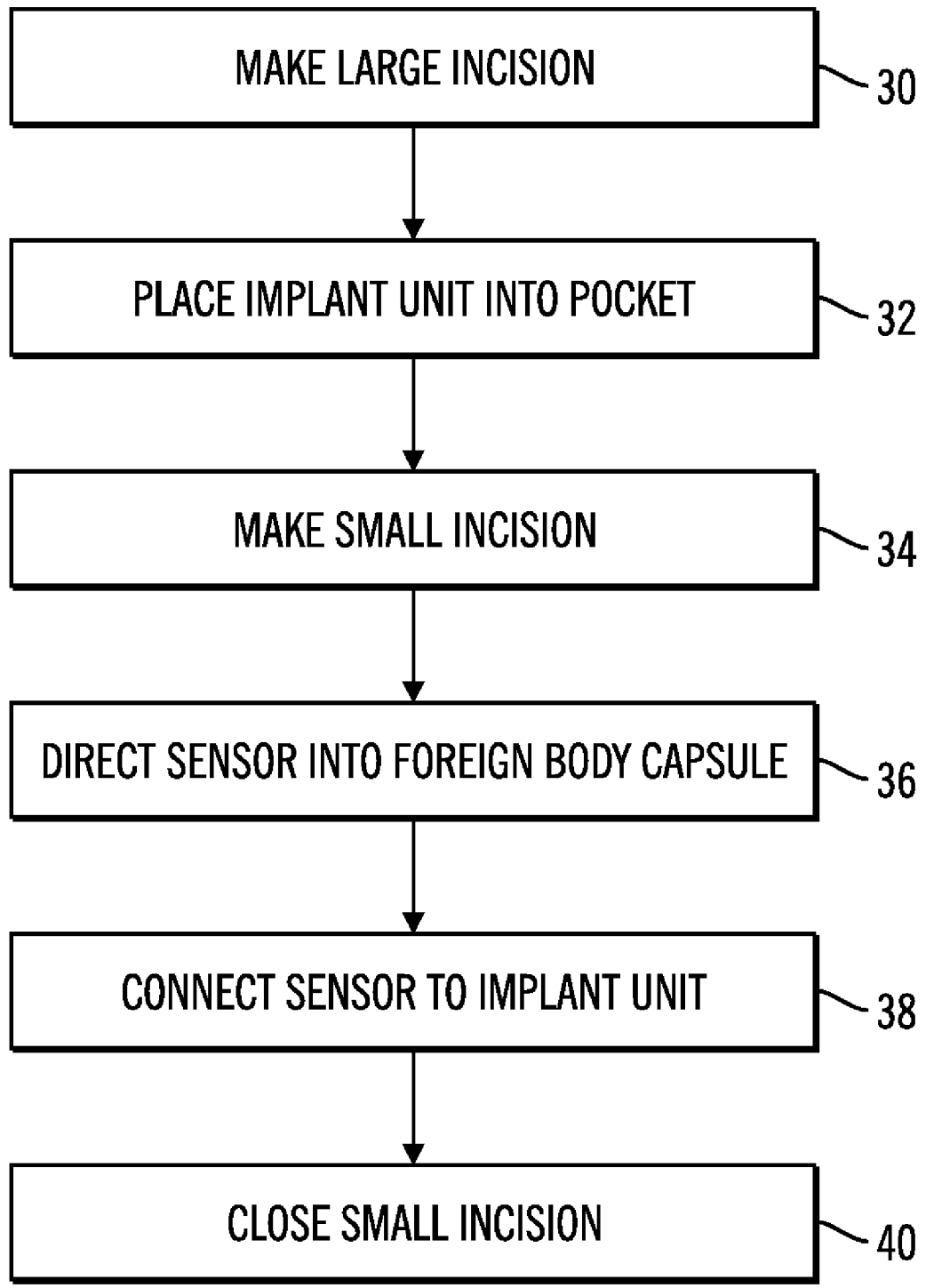
FIG. 3A shows a process for making a non-vascular placement of a sensor into a foreign body capsule according to an embodiment of the present invention

FIG. 3A shows a process for making a non-vascular placement of the sensor 12 into a foreign body capsule according to an embodiment of the present invention. At step 30, a large incision may be made in the body at a desired or convenient location for the implant unit 10. While making the incision of step 30, a pocket may be made in the subcutaneous tissue that is large enough to support the implant unit 10. At step 32, the implant unit 10 may be inserted into the subcutaneous tissue pocket. The pocket may then be closed.

Once the implant unit 10 has been inserted into the subcutaneous tissue pocket and the pocket has been closed, the implant unit 10 may be left in the body for a period of time long enough that a foreign body capsule forms around the implant unit 10. The implant unit 10 may need to be left undisturbed in its position in the body for up to several weeks, a month, or longer in order to allow the foreign body capsule to form. The foreign body capsule is made up of scar tissue, primarily collagen and fibrin.

During the period when the foreign body capsule is forming, a sensor 12 may or may not be attached to the implant unit 10. If a sensor 12 is not attached to the implant unit 10, it may still be possible to use the implant unit 10 in an open-loop configuration. For example, if the implant unit 10 contains telemetry circuitry, it may be possible to communicate with the implant unit 10 from a remote location. For example, if the implant unit 10 is an insulin pump, and no sensor 12 is attached to the implant unit 10 during the period in which the foreign body capsule is forming around the implant unit 10, the patient may still analyze his or her insulin levels by traditional methods, such as, for example, using a home analysis system to take a blood sample and analyze the levels of insulin in the blood. If it is determined that the patient needs a dosage of insulin, and if the insulin pump which has been placed into the patient's body is equipped with telemetry electronics, the patient may communicate with the insulin pump telemetrically using a portable transmitting unit and command the pump to deliver a dosage of insulin. Thus, the patient may begin to immediately use the insulin pump, without having a sensor 12 attached to the pump, in an open-loop configuration. Thus, using embodiments of the present invention, there is no need to wait for the foreign body capsule to form around the implant unit 10 before making use of the implant unit 10.

An oxygen sensor may be used in the vicinity of the foreign body capsule to determine if the foreign body capsule has formed and the area has healed. Generally, no oxygen will be detected during formation of the foreign body capsule.

Once the foreign body capsule has formed around the implant unit 10, at step 34 a small incision may be made in the vicinity of the implant unit 10 pocket allowing access to the receptacle 16 of the implant unit 10. If a sensor has been previously connected to the implant unit 10, it may be disconnected at this time. After the small incision has been made and any previously connected sensors have been disconnected from the implant unit, at step 36 the sensor 12 may be directed into the foreign body capsule. The sensing element 22 may be introduced into the foreign body capsule surrounding the implant unit through the small incision made at step 34. The sensing element 22 may be placed within the foreign body capsule. The connector 18 may reside in the subcutaneous pocket created for the implant unit 10 by the body.

In addition, a silicone plug may be used to plug the receptacle so that it remains open during the period of time the foreign body capsule is forming around the implant unit. If a silicone plug has been inserted into the receptacle 16, it may also be removed at this time.

At step 38, the sensor 12 may be connected to the implant unit 10 at the receptacle 16 on the implant unit 10 designed for connecting to the sensor 12 by connecting the connector 18 to the receptacle 16. Once the sensor 12 has been connected to the implant unit 10, the small incision may be closed at step 40. At this point, the implant unit 10 and the sensor 12 may be used in a closed-loop configuration. For example, if the implant unit 10 is an insulin pump and the sensing element 22 of the sensor 12 contains a glucose oxidase enzyme for sensing glucose and oxygen in order to determine insulin levels in the patient, the glucose and oxygen levels and, consequently, the insulin levels in the patient may be determined by the sensing element 22 in the foreign body capsule. Vascular placement of the sensor 12 is not required.

Figure 3B:
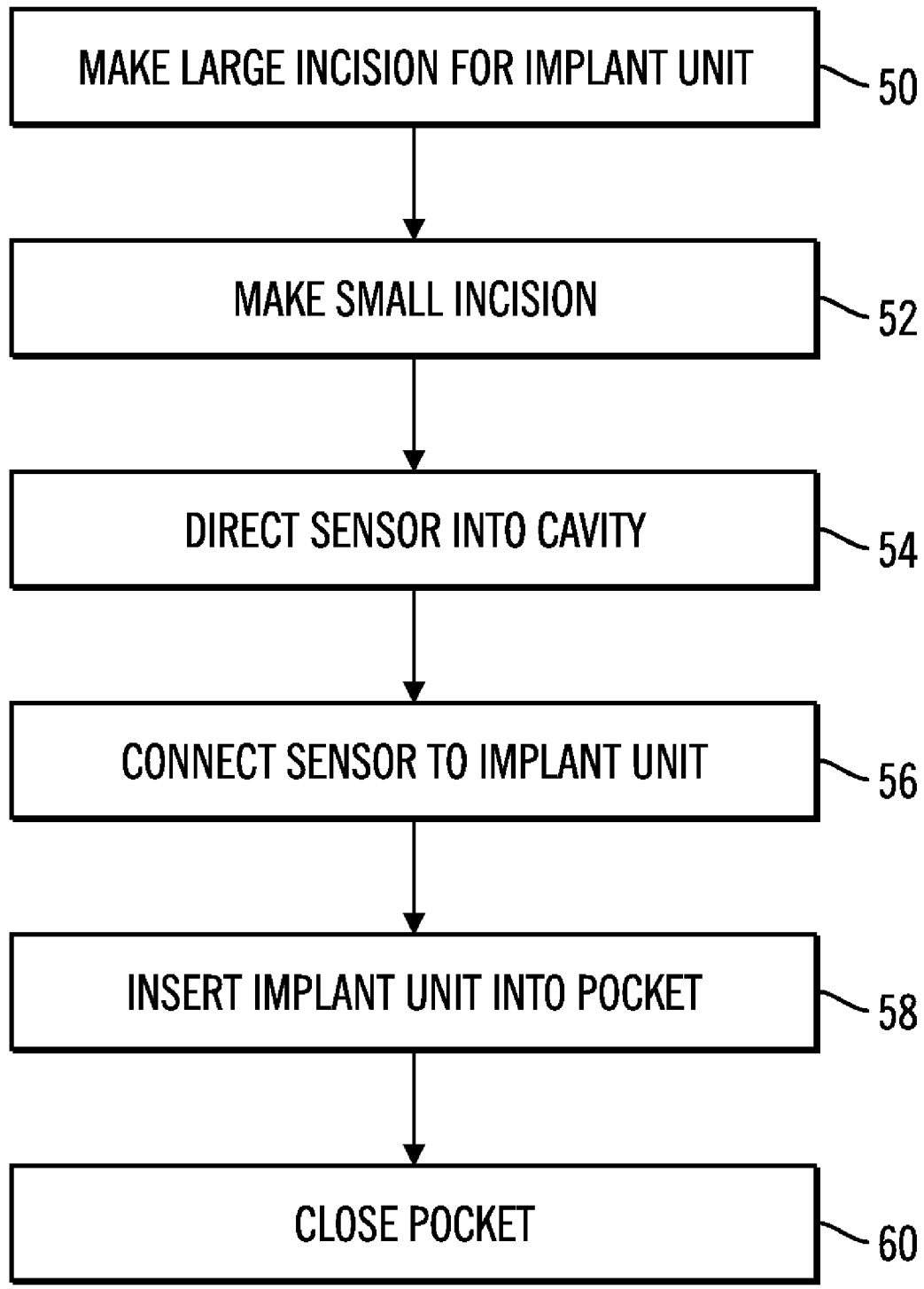
FIG. 3B shows a process for making a non-vascular placement of a sensor into a body cavity such as, for example, the peritoneal space, according to an embodiment of the present invention.

FIG. 3B shows a process for making a non-vascular placement of the sensor 12 into a body cavity such as, for example, the peritoneal space, according to an embodiment of the present invention. At step 50, a large incision may be made in the body at a desired or convenient location for the implant unit 10. While making the incision of step 50, a pocket may be made in the subcutaneous tissue above the cavity to be used that is large enough to support the implant unit 10.

After the large incision has been made for the implant unit 10 at step 50, at step 52 a small incision may be made in a muscle wall of the cavity such as, for example, the peritoneal space, for allowing implantation of the sensor 12. The small incision may be far or remote from final placement of the sensor 12. After the small incision has been made, at step 54 the sensor 12 may be directed into the cavity. The sensing element 22 may be introduced into the cavity through the small incision made at step 52. The connector 18 may reside in the subcutaneous pocket created for the implant unit 10 by the body.

At step 56, the sensor 12 may be connected to the implant unit 10 at the receptacle 16 on the implant unit 10 designed for connecting to the sensor 12 by connecting the connector 18 to the receptacle 16. Once the sensor 12 has been connected to the implant unit 10, at step 58 the implant unit 10 may be inserted into the subcutaneous tissue pocket created at step 50. After the implant unit 10 has been inserted into the subcutaneous tissue pocket, the pocket may be closed at step 60. As before, at this point the implant unit 10 and the sensor 12 may be used in a closed-loop configuration.

Figure 3C:
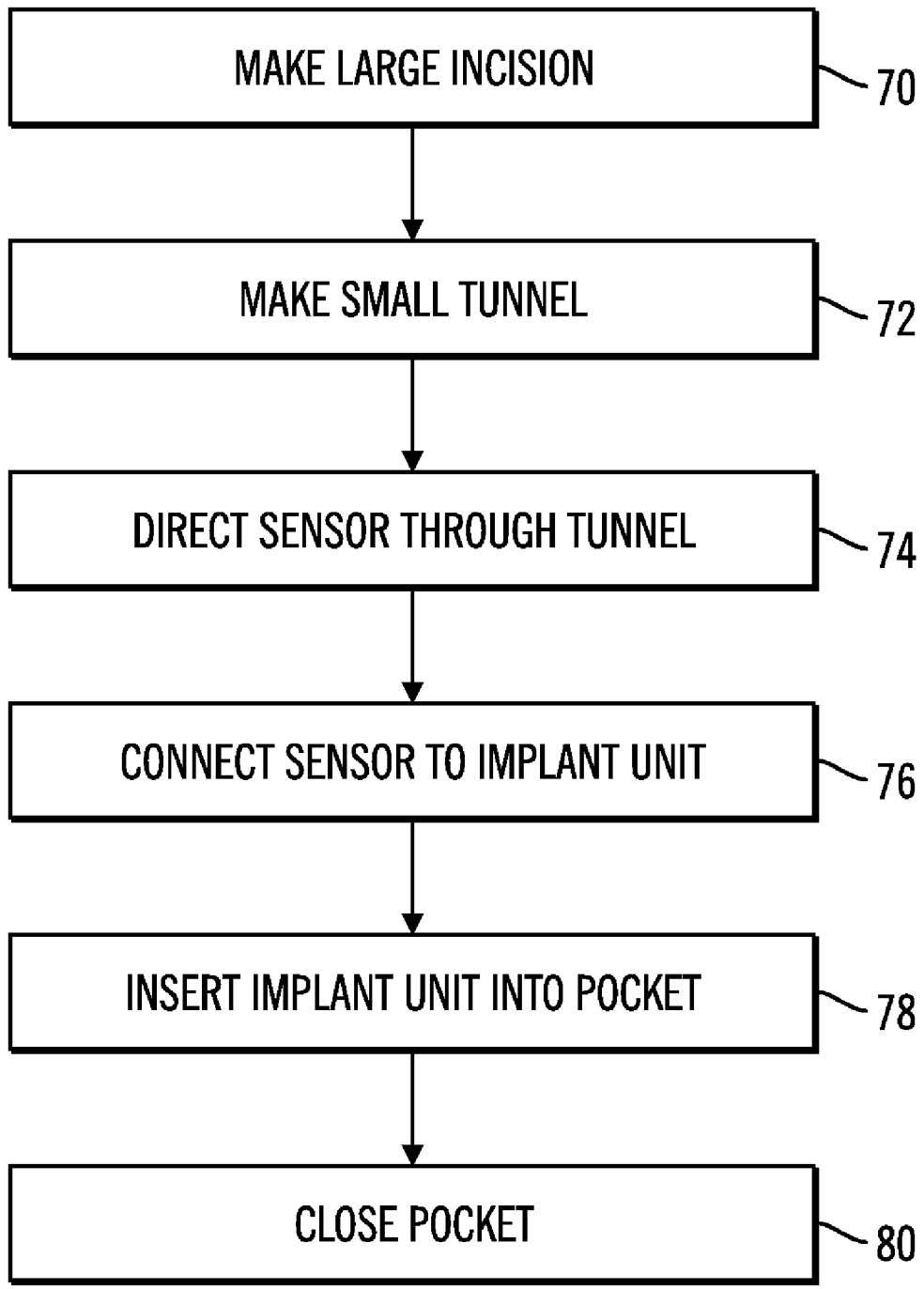
FIG. 3C shows a process for making a non-vascular placement of a sensor into subcutaneous tissue according to an embodiment of the present invention.

FIG. 3C shows a process for making anon-vascular placement of the sensor 12 into subcutaneous tissue according to an embodiment of the present invention. At step 70, a large incision may be made in the body at a desired or convenient location for the implant unit 10. While making the incision of step 70, a pocket may be made in the subcutaneous tissue above the cavity to be used that is large enough to support the implant unit 10.

After the large incision has been made for the implant unit 10 at step 70, at step 72 a small tunnel may be made for the sensor at the edge of pocket created for the implant unit 10. An incision for the tunnel may be made far or remote from final placement of the sensor 12. The tunnel may be made using a blunt, minimally traumatic tissue implant. The sensor 12 may be tunneled through the subcutaneous tissue by starting at an edge of the implant unit 10 pocket and tunneling into the subcutaneous tissue parallel to the skin. It may be desirable to stay within the subcutaneous tissue while tunneling. If the blunt, minimally traumatic tissue implant device used includes an introducer, the introducer may be left in the subcutaneous tissue while the remaining portion of the blunt, minimally traumatic tissue implant device may be removed.

After the tunnel has been made, at step 74 the sensing element 22 of sensor 12 may be directed into the introducer of the blunt, minimally traumatic tissue implant device. The connector 18 may reside in the subcutaneous pocket created for the implant unit 10 by the body. If it is desired that the sensor be fixed in its location, suture tabs such as, for example, those used on pacing leads or long term catheters may be used.

At step 76, the sensor 12 may be connected to the implant unit 10 at the receptacle 16 on the implant unit 10 designed for connecting to the sensor 12 by connecting the connector 18 to the receptacle 16. Once the sensor 12 has been connected to the implant unit 10, at step 78 the implant unit 10 may be inserted into the subcutaneous tissue pocket created at step 70. After the implant unit 10 has been inserted into the subcutaneous tissue pocket, the pocket may be closed at step 80. As before, at this point the implant unit 10 and the sensor 12 may be used in a closed-loop configuration.

The blunt, minimally traumatic tissue implant device used to tunnel the sensor 12 into a subcutaneous region may be a biopsy trocar 90 shown generally in FIG. 4. As shown in FIG. 4, the biopsy trocar 90 includes an introducer 92 into which the main body 94 of the trocar 90, having a sharp end 100, and a secondary body 96 of the trocar 90, having a blunt end 98, may be inserted. The introducer 92 may be made of plastic while the main body 94 and the secondary body 96 may be made of metal. The secondary body 96 having the blunt end 98 may be inserted into the main body 94 having the sharp end 100, and both the secondary body 96 and the main body 94 may be inserted into the introducer 92. All three portions of the trocar 90 may then be tunneled into the subcutaneous tissue. The sharp end 100 of the main body 94 of the trocar 90 may make an initial incision, while the blunt end 98 of the secondary body 96 may tunnel through the subcutaneous tissue. By tunneling through the subcutaneous tissue with the blunt end 98 of the secondary body 96, less damage occurs to the subcutaneous tissue than would occur if the subcutaneous tissue were tunneled with the sharp end 100 of the main body 94, resulting in less bleeding and less trauma to the tissue and the patient. Once the end of the trocar 90 has reached the desired location for the sensing element 22 of the sensor 12, the main body 94 and the secondary body 96 are removed from the introducer 92. The sensor 12 is then guided through the introducer 92 so that the sensing element 22 eventually arrives at its desired location. The introducer 92 may then be removed from the body and the connector 18 may then be connected to the implant unit 10. Because the sensing element 22 of the sensor 12 is not located in the vicinity of the main incision that was made to insert the implant unit 10, the difficulties associated with obtaining a signal from the sensing element 22 due to the trauma of the area are avoided. Because the sensing element 22 is located away from the implant unit 10 incision, there is nothing to prevent obtaining a signal from the sensing element 22 in a very short period of time. For example, after the sensor 12 has been tunneled into the subcutaneous tissue and connected to the implant unit 10, it may possible to obtain a signal from the sensing element 22 within 24 hours of sensor 12 placement. Thus, for example, if the implant unit 10 is an insulin pump and the sensing element 22 of the sensor 12 is a glucose oxidase enzyme for sensing insulin levels in diabetics, automated insulin analysis and insulin delivery in a diabetic patient may be feasible within 24 hours of in vivo implantation of the implant unit 10 and the sensor 12.

If so desired, a variety of materials may be placed around the implant unit 10 or sensor 12 to promote different characteristics of the foreign body capsule or sensor area. For example, if it is desired to grow more blood vessels in the area of the foreign body capsule or sensor 12, the implant unit 10 or sensor 12 may be covered with GORE-TEX or PTFE. Other materials may also be used to cover the implant unit 10 or sensor 12 depending on the nature of the characteristics of the foreign body capsule or area around the sensor 12 desired. In addition, various chemicals may be pumped into the area of the foreign body capsule in order to promote different characteristics of the foreign body capsule, such as, for example, blood vessel growth.

The implant unit 10 and the sensor 12 are modular units and may connect to each other via a mechanical interface. Because of the modularity of the implant unit 10 and the sensor 12, the sensor 12 may be removed or replaced without removing the implant unit 10. Thus, due to the small size of the sensor 12, only a small incision is required and trauma to the patient is minimized. No large incision is necessary to remove the implant unit 10 unless the implant unit 10 itself needs to be removed or replaced.

Figure 5A:
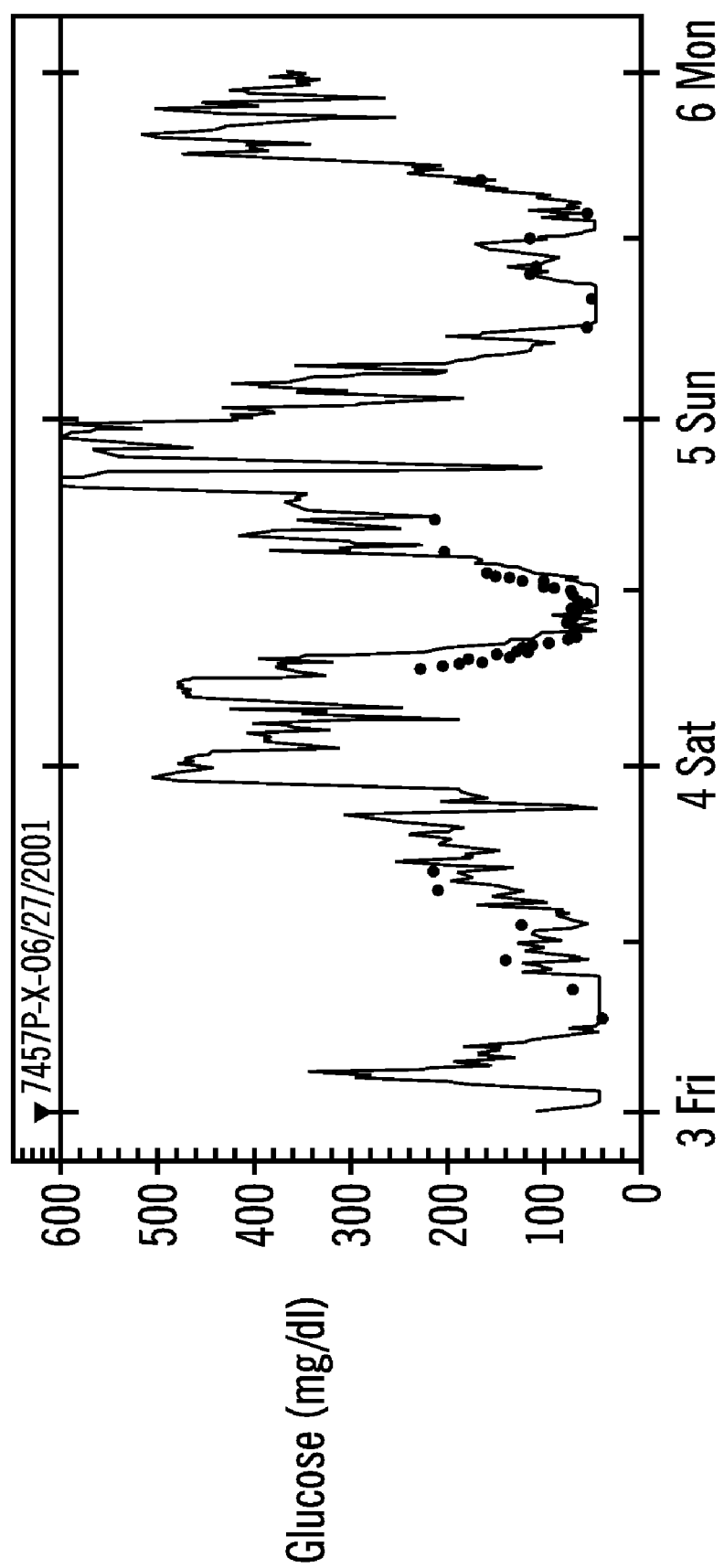
FIG. 5A shows glucose data over a period of several days for a sensor implanted into a foreign body capsule according to an embodiment of the present invention.
Figure 5B:
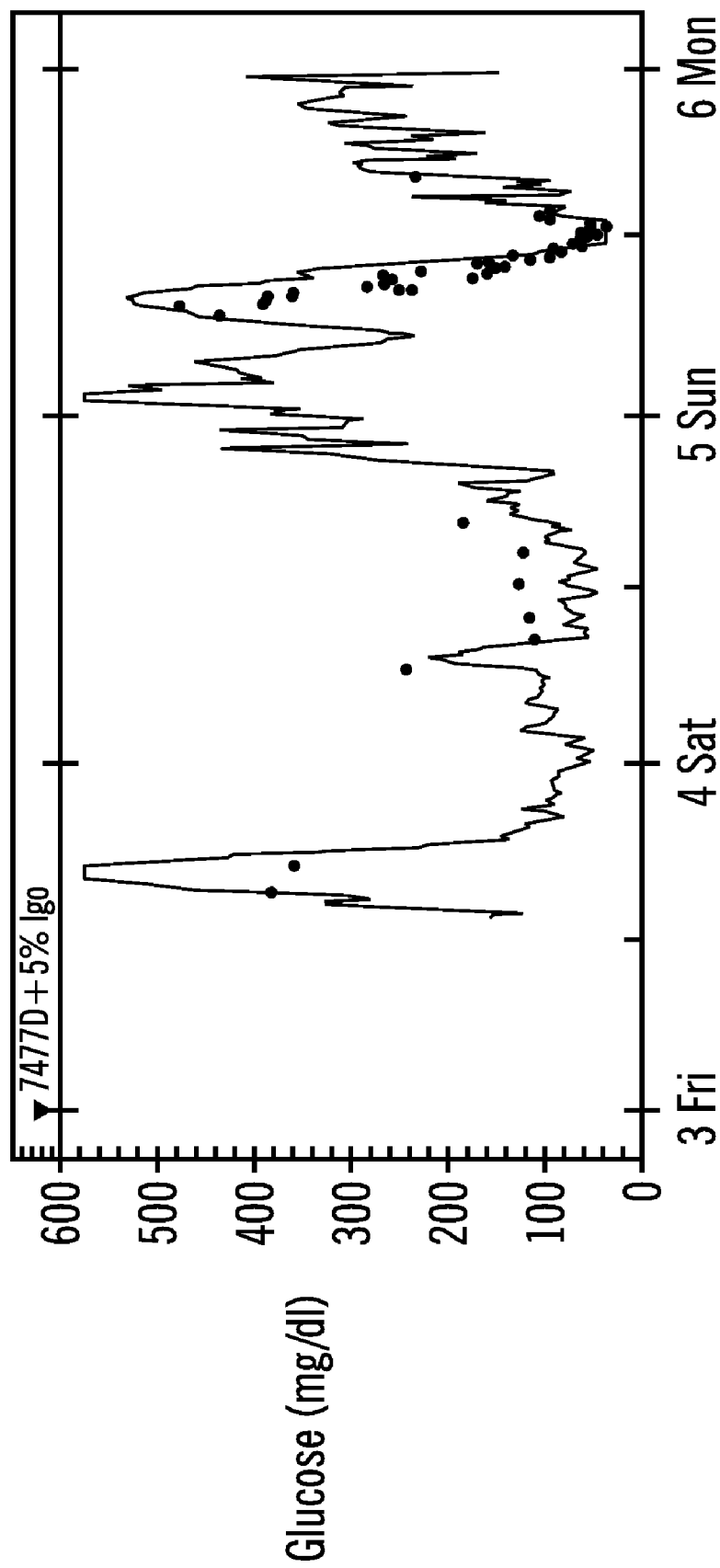
FIG. 5B shows glucose data over a period of several days for a sensor implanted into subcutaneous tissue according to an embodiment of the present invention.
Figure 5C:
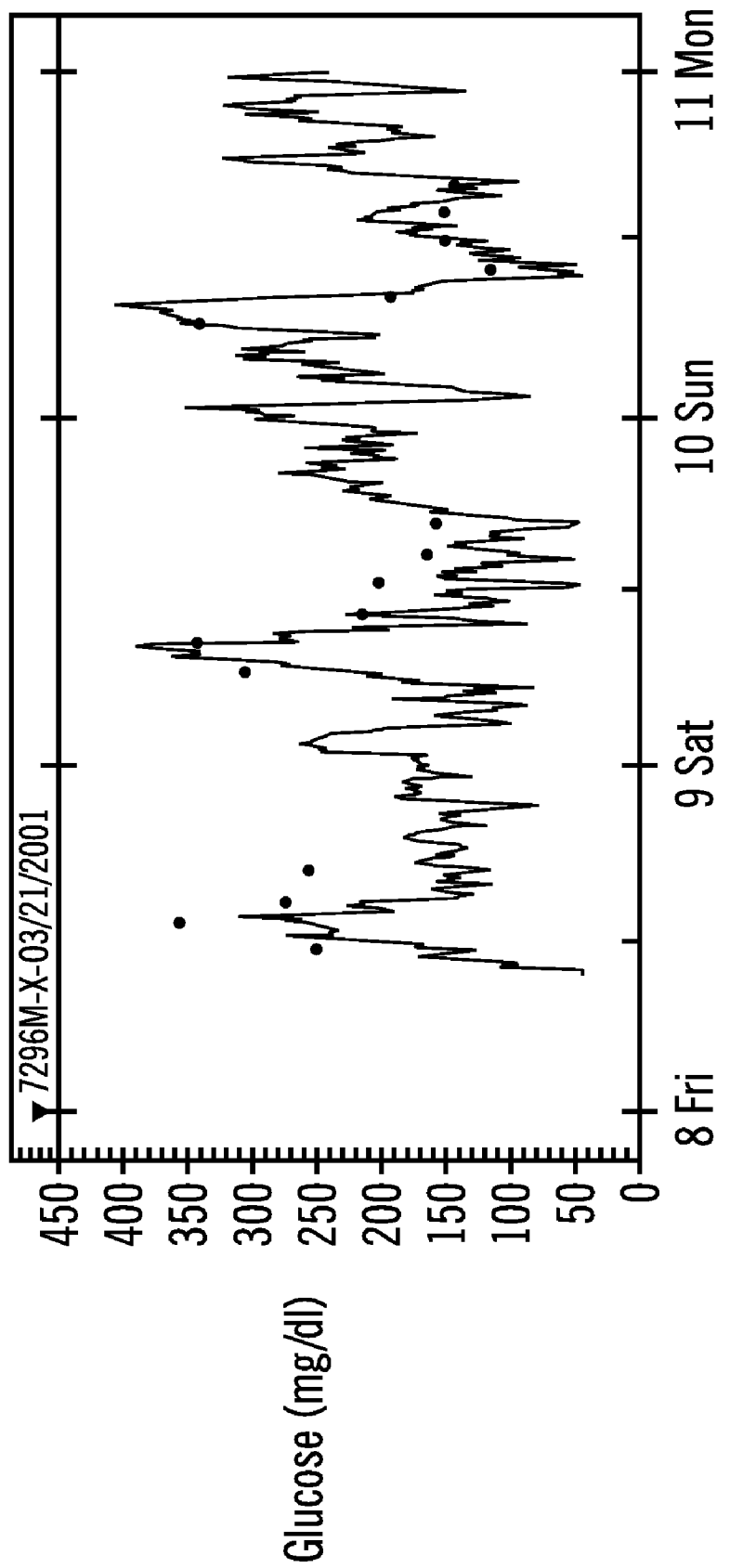
FIG. 5C shows glucose data over a period of several days for a sensor implanted into a body cavity such as a peritoneal space according to an embodiment of the present invention.

Data for sensors used in glucose sensing applications may be seen in FIGS. 5A, 5B and 5C. In FIG. 5A, glucose data over a period of several days for a sensor implanted into a foreign body capsule may be seen. In FIG. 5B, glucose data over a period of several days for a sensor implanted into subcutaneous tissue may be seen. In FIG. 5C, glucose data over a period of several days for a sensor implanted into a body cavity such as a peritoneal space may be seen.

According to another embodiment of the present invention, a physiological parameter sensing element may be placed in any medical article or device that has surfaces that contact tissue, blood, or other bodily fluids in the course of their operation, which fluids are subsequently used in patients. This may include, for example, extracorporeal devices for use in surgery such as blood oxygenators, blood pumps, tubing used to carry blood and the like which contact blood which is then returned to the patient.

Figure 6:
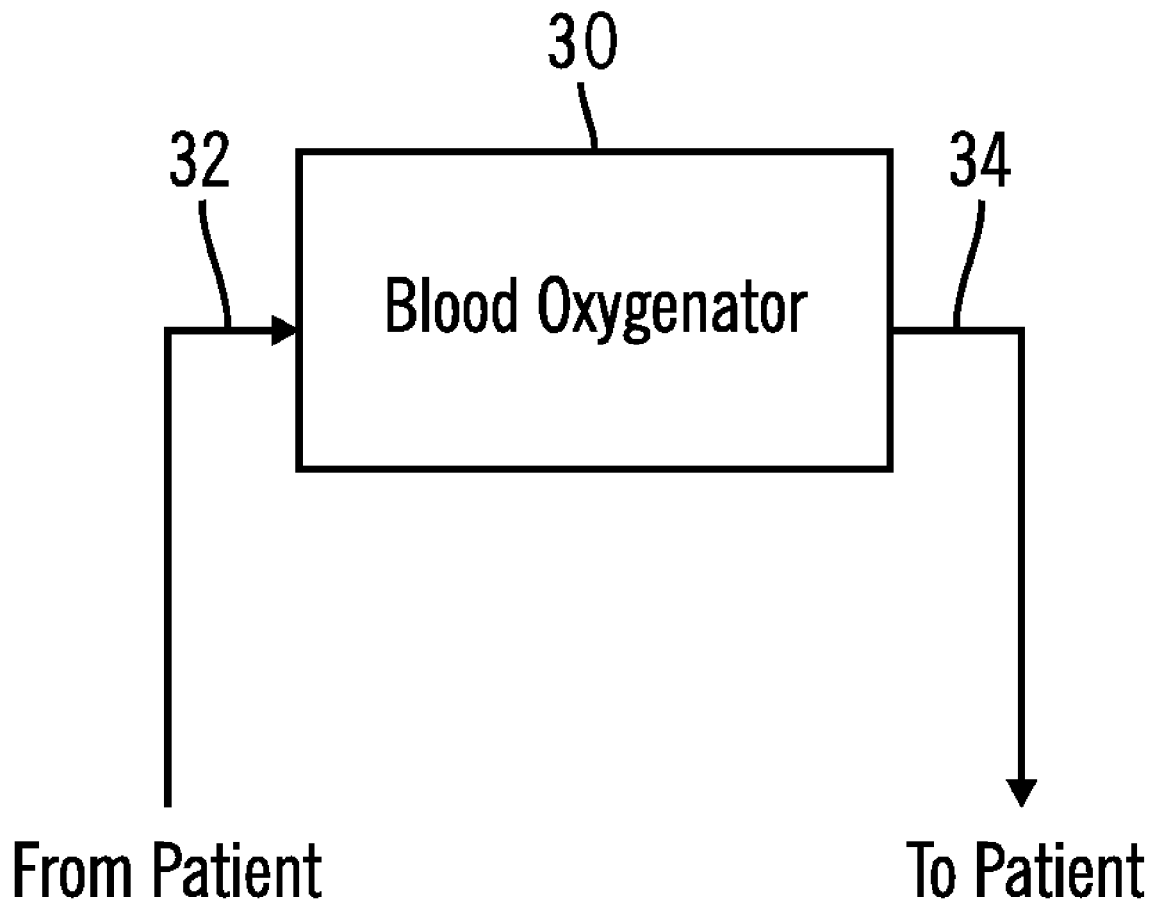
FIG. 6 shows a blood oxygenator in which a sensing element may be placed, according to an embodiment of the present invention.

FIG. 6 shows a blood oxygenator 30. Blood oxygenators are well known in the medical field. Usually they are disposable components of so-called "heart-lung machines." These machines mechanically pump a patient's blood 32 and oxygenate the blood during major surgery such as a heart bypass operation. The oxygenated blood 34 is then returned to the patient.

The physiological parameter sensing element may be placed in the blood oxygenator 30 in order to detect oxygen or other physiological parameters in the patient's blood. Alternatively, the physiological parameter sensing element may be placed in an input line which feeds the patient's blood 32 to the blood oxygenator 30 or an output line that delivers the oxygenated blood 34 to the patient. In this manner, the physiological parameter sensing element may sense a physiological parameter in the blood.

Other embodiments of the present invention address the problems described above in relation to the placement of a sensor in non-vascular areas of a body. As discussed above, when the sensing element is used in a vascular area of the body, the sensing element senses an homogenous amount of oxygen or other physiological parameter as it flows past the sensing element. However, the amount of a physiological parameter in non-vascular areas of the body may be more heterogeneous. In such a case, the sensing element may sense the physiological parameter through diffusion from, for example, fluid around the sensing element.

Thus, when the sensing element is located in non-vascular areas of the body, the heterogeneous nature of a physiological parameter in that area may result in varying amounts of the physiological parameter. In other words, the amount of a physiological parameter sensed may vary depending on the location of the sensing element within that particular area of the body. As an example, when the particular area of the body is the peritoneum and the physiological parameter is oxygen, the capillaries of the peritoneum are the sources of the oxygen. The topology of capillaries within the peritoneum may vary in different areas of the peritoneum. Thus, the oxygen levels may also vary in different areas of the peritoneum.

Therefore, using only one sensing element it may be difficult to accurately determine an "overall amount" of the physiological parameter in the non-vascular areas of the body, i.e., an amount that accurately represents, for example, an average amount or other suitable statistical measure of the physiological parameter in the particular area of the body. This is because the amount of the physiological parameter may vary depending on the location of the sensing element in the particular area of the body. In addition, another problem results from the fact that the heterogeneous nature of the physiological parameter being sensed by the sensing element may induce noise in the signal obtained from the sensing element.

Figure 7:
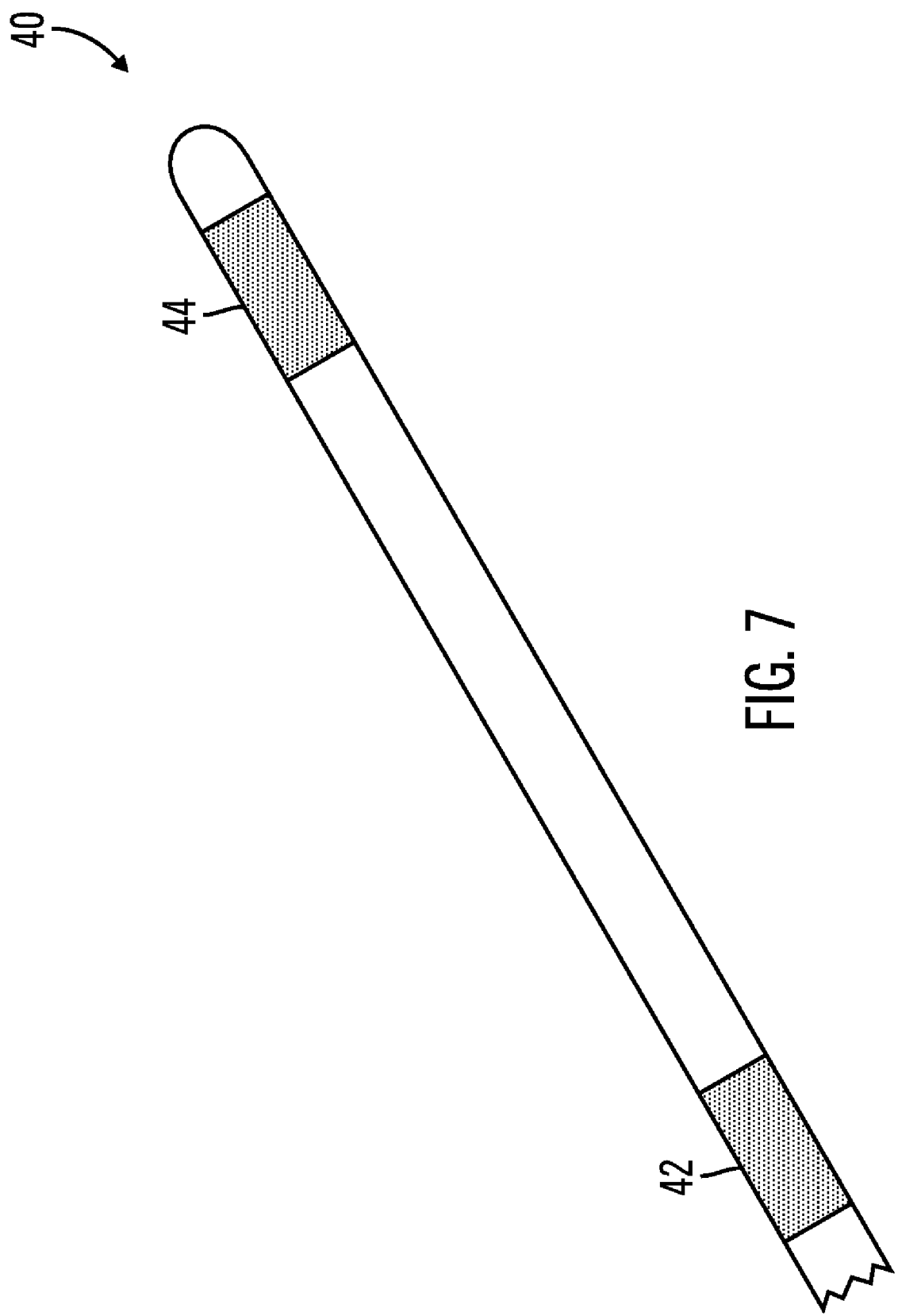
FIG. 7 shows a sensor lead including two sensing elements according to an embodiment of the present invention.

In order to more accurately determine the overall amount of the physiological parameter in a particular area of the body and to reduce the amount of noise in the obtained signal, according to another embodiment of the present invention shown in FIG. 7, sensor lead 40 may include two or more sensing elements. As shown in FIG. 7, one sensing element may be a proximal sensing element 42, i.e., one located closest to an end of the sensor lead 40 that is attached to the implant unit 10. The other sensing element may be a distal sensing element 44, i.e., one located closest to an end of the sensor lead 40 furthest away from the point of attachment of the sensor lead 30 to implant unit 10. In other embodiments, there may be further sensing elements located between the proximal sensing element 42 and the distal sensing element 44. In some embodiments, the distance between one sensing element and another sensing element may be approximately 5 or 6 inches. However, the distance between sensing elements may vary depending on the particular application in which the sensing elements are used, as well as the location of the sensing elements.

The spatial separation of sensing elements 42, 44 in sensor lead 40 is employed in order to sense the physiological parameters at different locations within the environment in which the sensor lead 40 is situated. For example, the sensing elements 42, 44 may be situated within the peritoneum and the physiological parameter to be sensed may be oxygen. By employing two or more sensing elements that are separated along the sensor lead 40, each of the sensing elements may generate a signal representing an amount of oxygen at different spatial points within the peritoneum. Thus, at any one time, or in succession within a given time period, signals representing sensed amounts of oxygen may be taken from the two or more sensing elements. The individual sensed amounts of oxygen may then be used to determine an overall amount of the physiological parameter.

This may be done, as an example, through use of an algorithm or algorithms which determine the overall amount based on the individual sensed amounts at the different locations within the environment. The algorithm or algorithms, for example, may determine the overall amount of the physiological parameter by calculating a statistical measurement of the individual sensed amounts represented by the generated signals. The statistical measurement may be, but is not limited to, a maximum amount for the individual sensed amounts, an average amount of the individual sensed amounts, a median of the individual sensed amounts, an arithmetic mean of the individual sensed amounts, or a weighted arithmetic mean of the individual sensed amounts.

The algorithm may be executed, for example, by a computing element comprising software, hardware, firmware or a combination of software, hardware, and firmware. In one embodiment, the computing element for executing the algorithm or algorithms may be implemented by electronics within an implant unit associated with the sensing elements 42 and 44, such as the electronics in implant unit 10 described above. In alternative embodiments the sensing elements may be used in or with an extracorporeal device such as a blood oxygenator and the algorithm or algorithms may be executed by a computing element associated with the extracorporeal device or by a dedicated computing element associated with the sensing elements.

Figure 8:
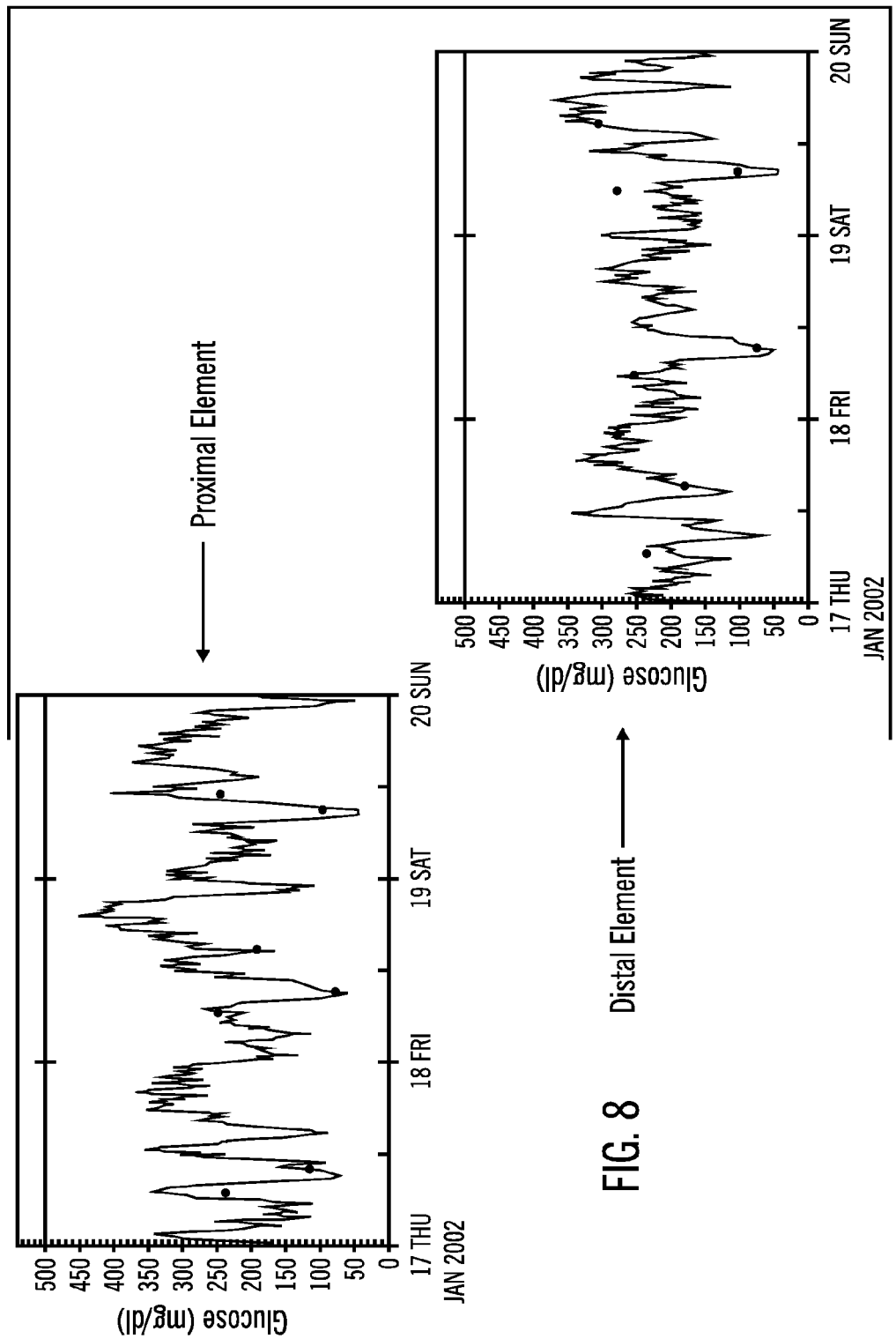
FIG. 8 shows a graphical representation of glucose data over a period of several days for each of two sensing elements of a sensor lead implanted into the peritoneum according to an embodiment of the present invention.

As discussed above, the variance of oxygen levels may induce noise in the individual sensing elements 42, 44 of the sensor lead 40. In FIG. 8, a graphical representation of glucose data over a period of several days may be seen for sensor lead 40 implanted into the peritoneum. The glucose data is shown for both the proximal sensing element 42 and the distal sensing element 44. The glucose data was obtained by detecting a first and a second signal from the proximal sensing element 42 and the distal sensing element 44, respectively. The first and second signals represent, respectively, first and second individual amounts of glucose. As can be seen in FIG. 8, the first and second signals contain a first and a second noise level, respectively.

Figure 9:
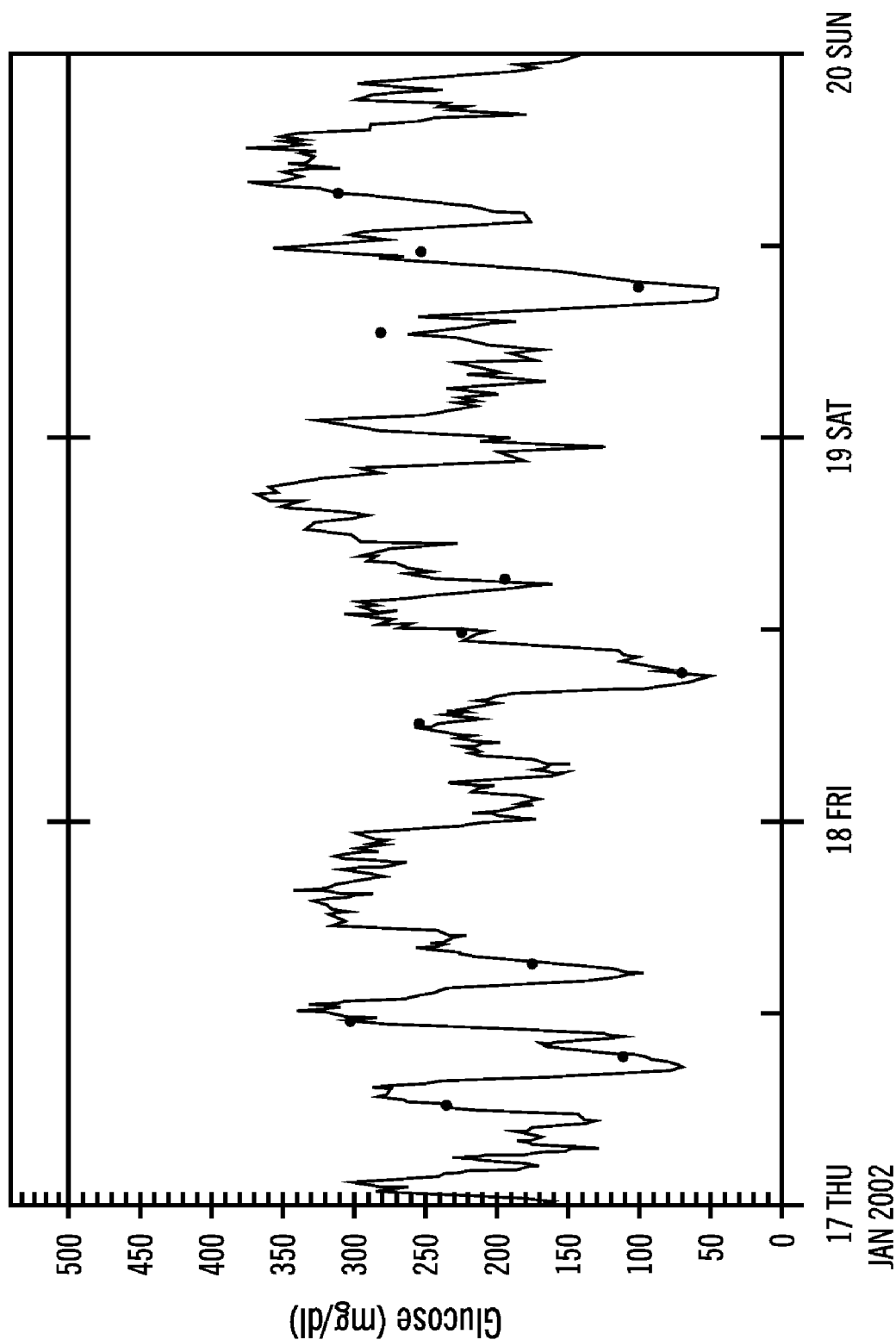
FIG. 9 shows a graphical representation of the average of the glucose data for the two sensing elements of FIG. 7 over the same period according to an embodiment of the present invention.

In FIG. 9, a graphical representation of glucose data over the same period for both the distal and proximal sensing elements is shown. The glucose data shown in FIG. 9 is a third signal representing an average amount of glucose calculated using the first and second signals representing individual sensed amounts of glucose. This average amount may be calculated using an algorithm, according to an embodiment of the present invention described above. As can be seen in FIG. 9, an average noise level of the third signal (a third noise level) is less than that of the first and second noise levels of the first and second signals, according to embodiments of the present invention. Thus, by averaging the output signals from two or more sensing elements, the noise level of the averaged signal produced by the sensing elements may be reduced, producing a smoother signal. Although the statistical measurement used to obtain the third signal above is an average amount of the individual sensed amounts, other statistical measurements may be used, including, but not limited to, a maximum amount for the individual sensed amounts, a median of the individual sensed amounts, an arithmetic mean of the individual sensed amounts, and a weighted arithmetic mean of the individual sensed amounts.

Although in FIG. 7 the sensing elements are shown in a one-dimensional straight line, the invention is not so limited. In fact, the benefit of multiple element spatial sensing may be realized using any geometry or array of sensing elements, including two and three-dimensional arrays. Furthermore, multiple element spatial sensing may be performed when the sensing elements are used in a vascular area of the body and is not restricted to use in the peritoneum or other non-vascular area.

According to embodiments of the present invention, digital signal processing may also be used either alone or in combination with a multiple element spatial sensing method according to embodiments of the present invention to reduce the noise level of the signal produced by the sensing elements, producing a smoother signal. A digital signal processor ("DSP") may use known noise reduction techniques such as filtering, as well as other signal smoothing techniques. The DSP may be located within an implant unit associated with the sensing elements 42 and 44, such as the implant unit 10. In alternative embodiments where the sensing elements are used in an extracorporeal device such as a blood oxygenator, the DSP may be associated with the extracorporeal device or may be a dedicated DSP associated with the sensing elements.

In addition, according to other embodiments of the invention, more aggressive frequency based filtering may be used either alone or in combination with the multiple element spatial sensing and/or digital signal processing to reduce the noise level. Thus, the central frequency of the noise may be determined and the filter may be used to cut off the noise at that frequency. In one embodiment, a single-pole IIR filter is used for this purpose. However, other filters may be used depending on the application.

Figure 10:
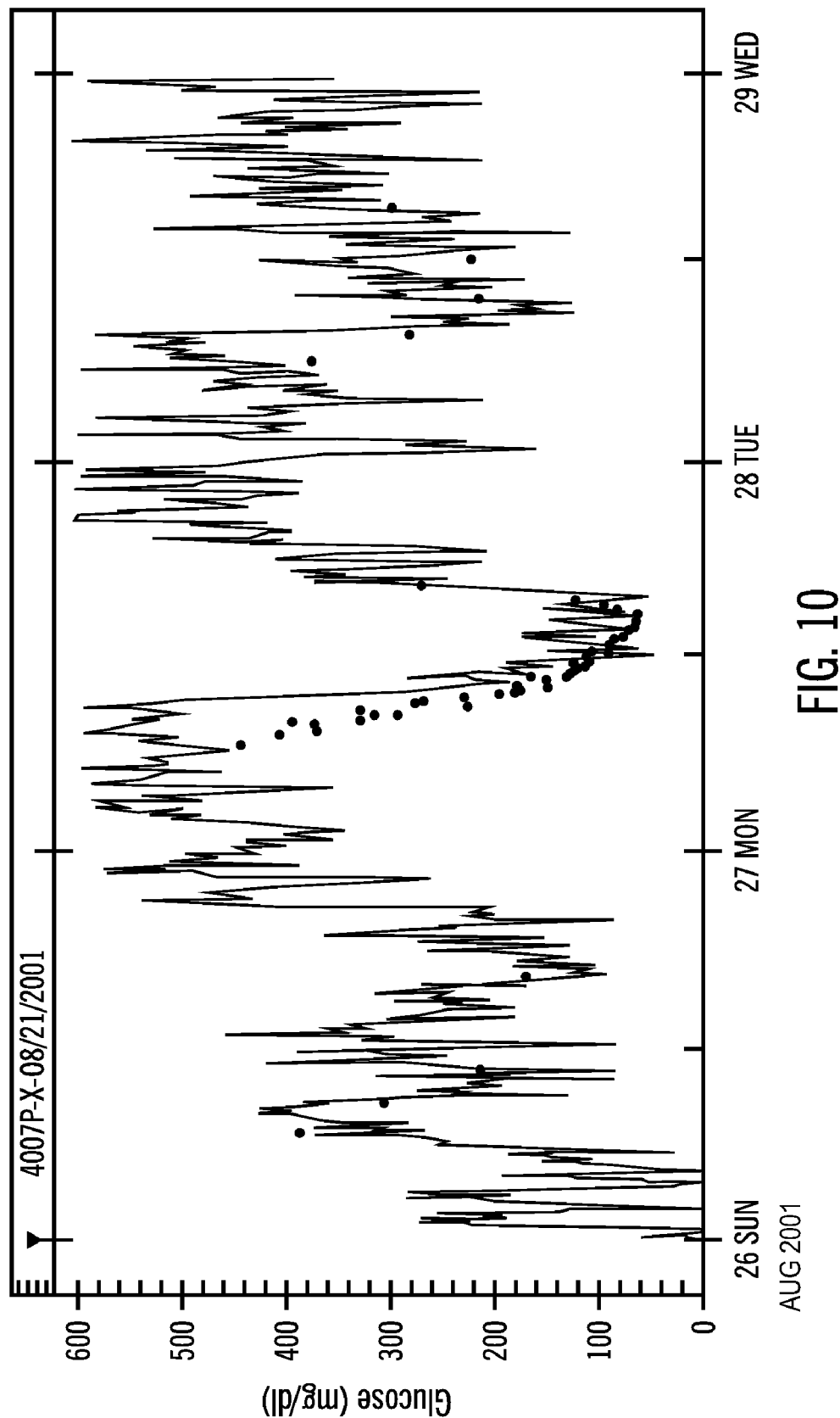
FIG. 10 shows a graphical representation of unfiltered glucose data over a period of several days for a sensing element of a sensor lead implanted into the peritoneum according to an embodiment of the present invention.
Figure 11:
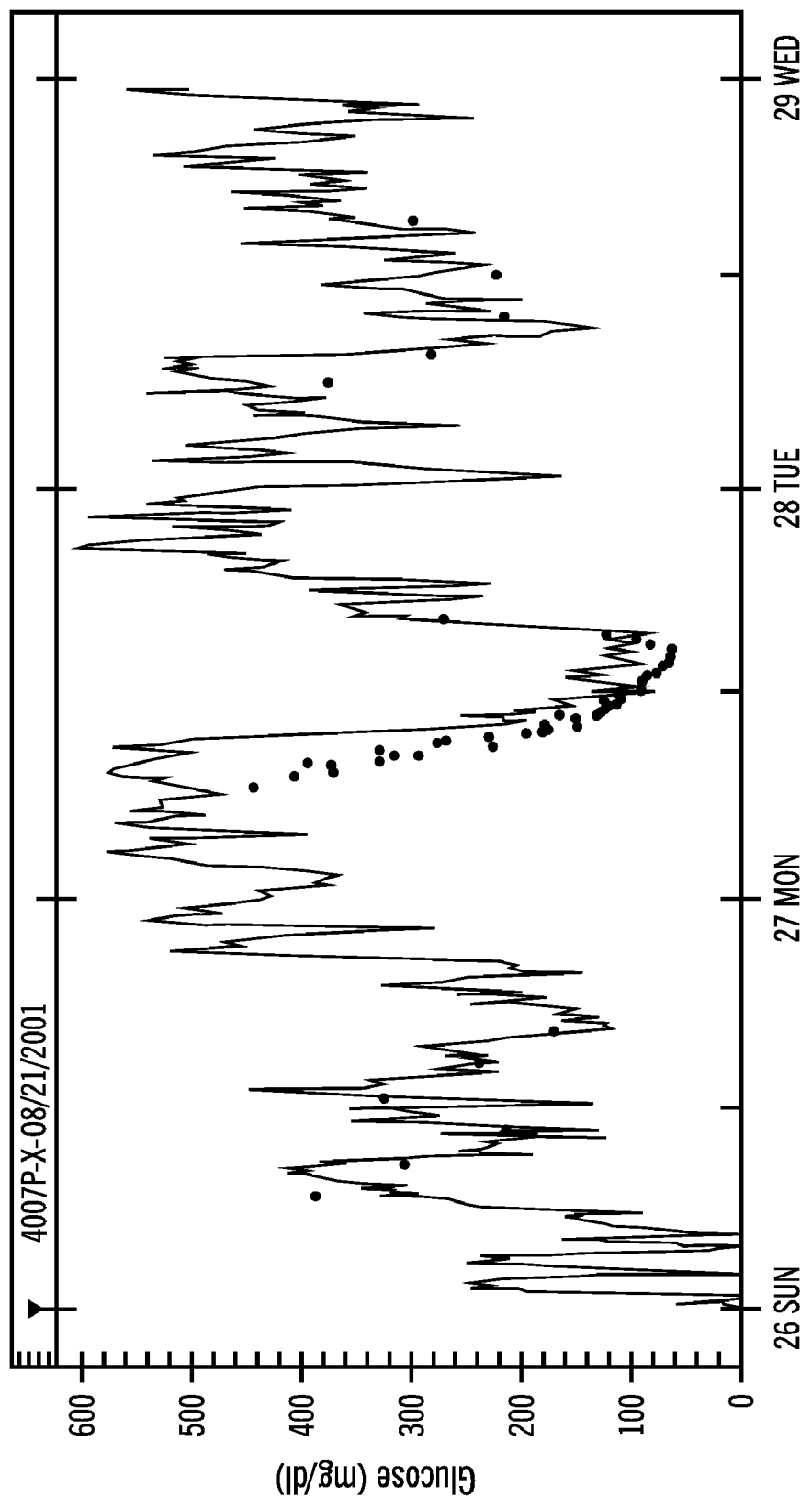
FIG. 11 shows a graphical representation of filtered glucose data for the sensing element of FIG. 10 over the same period according to an embodiment of the present invention.

In FIG. 10, a graphical representation of unfiltered glucose data over a period of several days may be seen for proximal sensing element 42 of sensor lead 40 implanted into the peritoneum. In FIG. 11, a graphical representation of filtered glucose data may be seen for proximal sensing element 42 over the same period. As can be seen in FIG. 11, the noise level of the signal produced by proximal sensing element 42 has been reduced by filtering the signal according to embodiments of the present invention.

Figure 12:
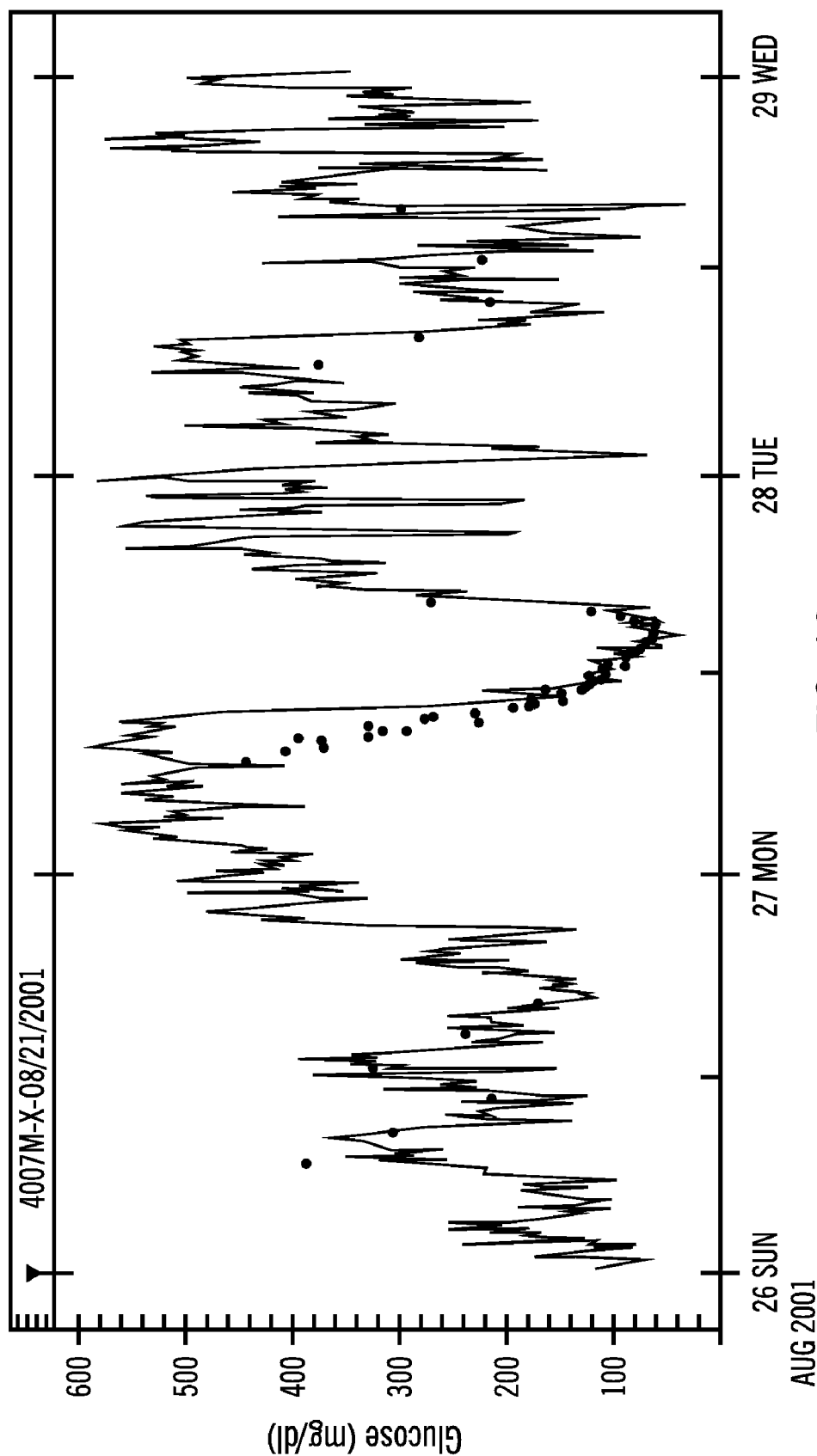
FIG. 12 shows a graphical representation of the unfiltered average of the glucose data for the two sensing elements of FIG. 7 over a period of several days according to an embodiment of the present invention.
Figure 13:
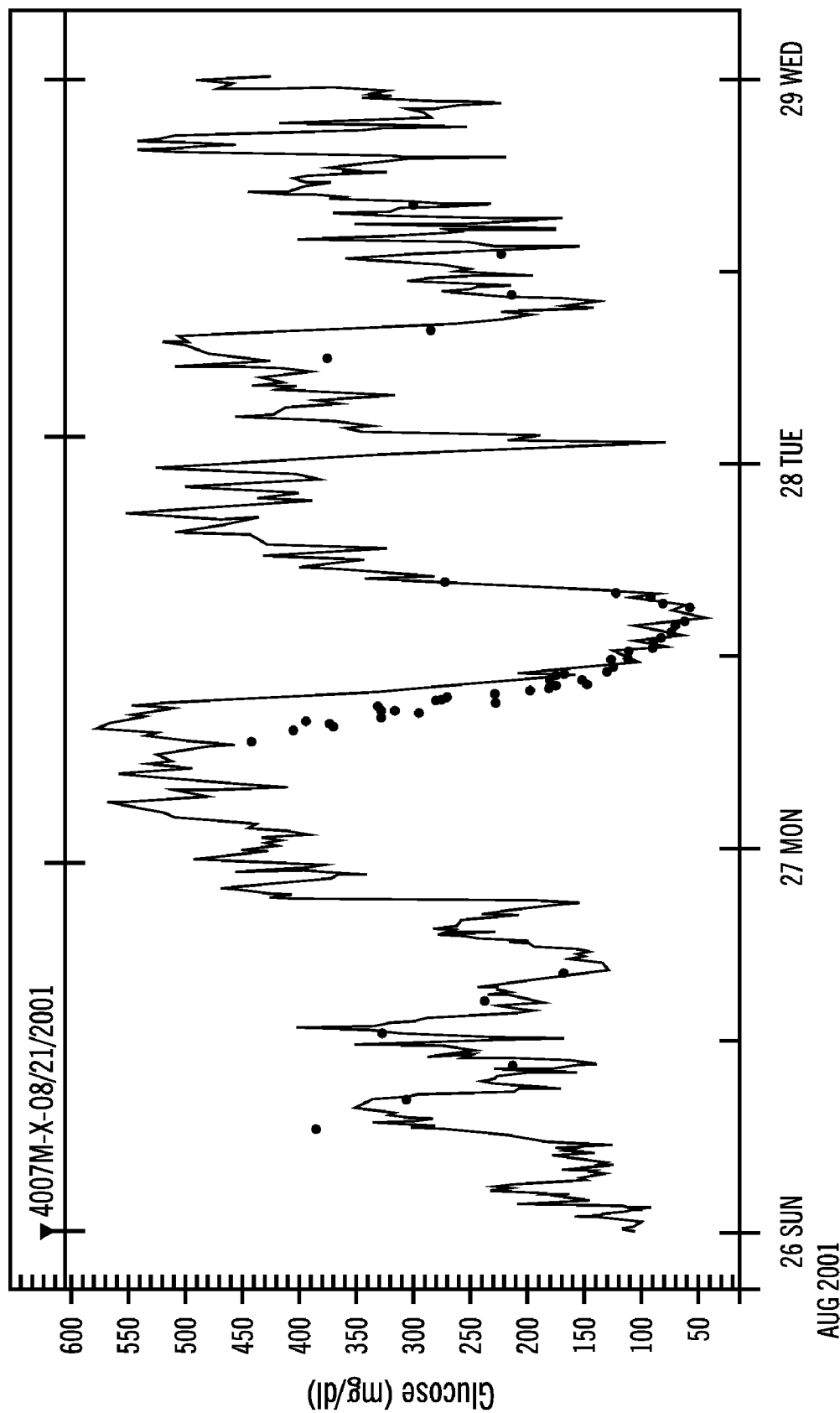
FIG. 13 shows a graphical representation of the filtered average of the glucose data for the two sensing elements of FIG. 7 over the same period according to an embodiment of the present invention.

In FIG. 12, a graphical representation of the unfiltered average of the glucose data over the same period for both the distal and proximal sensing elements is shown. In FIG. 13, a graphical representation of the filtered average of the glucose data over the same period for both the distal and proximal sensing elements is shown. As can be seen in FIG. 13, the noise level of the signal representing the average of the glucose data has been reduced by filtering the signal according to embodiments of the present invention.

According to other embodiments of the present invention, in vivo calibration may be used alone or in combination with the multiple element spatial sensing, digital signal processing and/or filtering to reduce the noise level.

Figure 14:
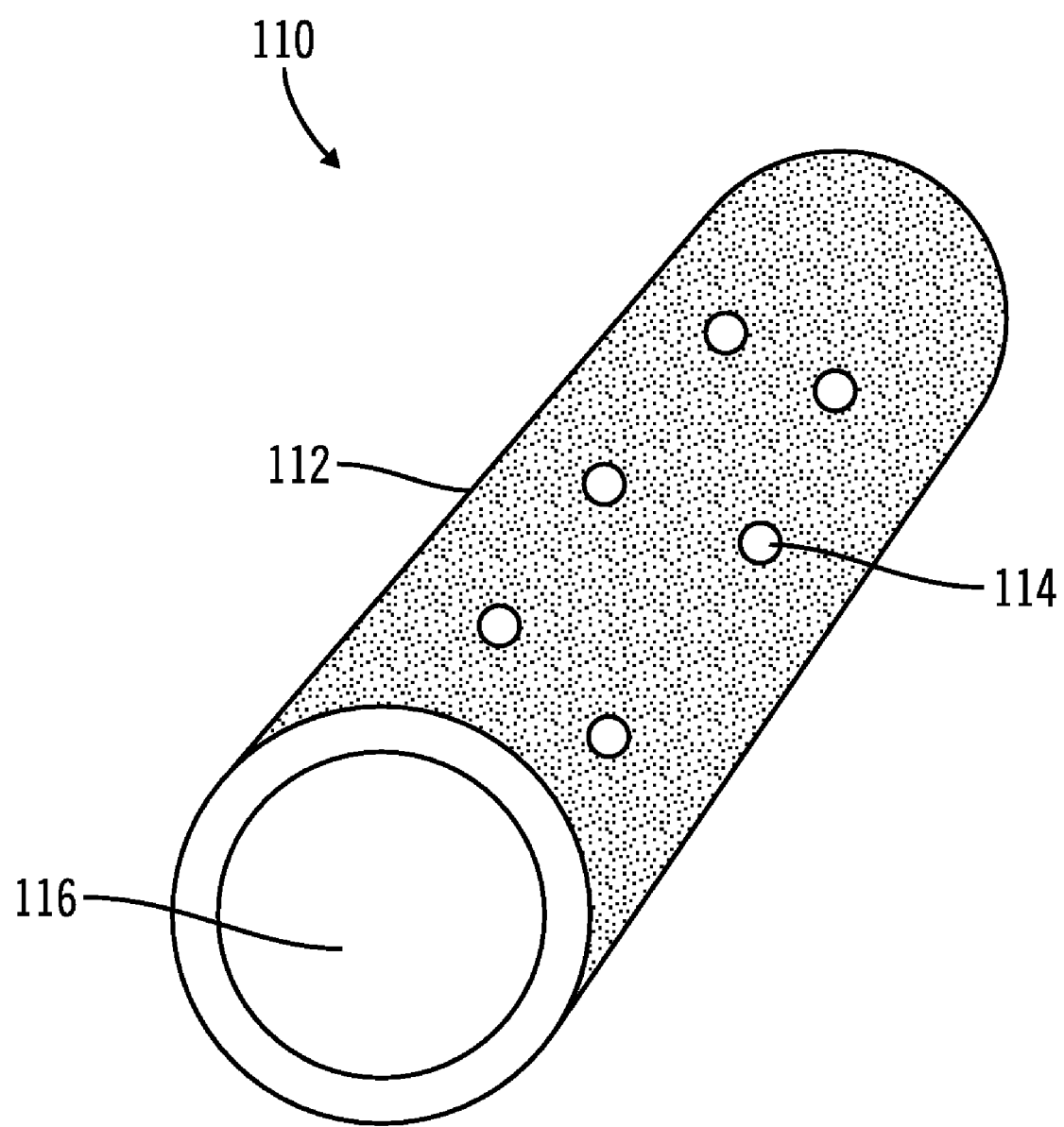
FIG. 14 shows a perspective view of a placement site structure according to an embodiment of the present invention.

A placement site structure 110 used to structurally engineer a sensor placement site according to an embodiment of the present invention is shown in FIG. 14. The placement site structure 110 may be viewed as a mechanical "scaffold" within a tissue mass around which forms a vascular bed in close proximity to the sensor. A sensor (not shown in FIG. 14) may be placed within an interior space 116 of the placement site structure 110, providing easy sensor removal and reinsertion into a non-vascular area of the body. The placement site structure 110 may be formed into a variety of shapes to accommodate any of a variety of sensors. In FIG. 14, the placement site structure 110 is formed as a right circular cylinder having an interior space 116. According to one embodiment of the invention, the placement site structure 110 may be a tube or a stent. In the embodiment shown, an interior diameter of the placement site structure 110 may be 0.010" to 0.030' greater than an outer diameter of the sensor. A layer of silicone rubber tubing 112 may surround the body of the placement site structure 110, except in a region of the sensor containing an opening to an enzyme electrode. The silicone rubber tubing 112 may provide a barrier for tissue ingress and may also provide direction for tissue growth between the outer surface of the sensor and inner surface of the placement site structure 110. Openings 114 in the placement site structure 110 may also be positioned about 0.60" away from a sensor electrode to facilitate tissue anchoring. Vascularization around the placement site structure 110 may be promoted by coating the silicone rubber tubing 112 with angiogenic factors or endothelial cells. Openings or holes 114 may be provided in the silicone rubber tubing 112 as an additional pathway to the implant site for angiogenic factors or plasmids which encode such factors. The size of the holes 114 may be in the mil or micron range. The holes 114 may also provide openings for tissue ingress into the area between the sensor and the interior walls of the placement site structure 110. Hole density and placement may be designed to satisfy both the need for tissue growth in the interior portion of the placement site structure 110 and the need to direct blood vessels feeding the tissue to the openings of the placement site structure 110 closest to the sensor electrodes. The opening 114 in the placement site structure 110 near the sensor electrodes may be exposed to an infusion of angiogenic factors, plasmids encoding for angiogenic factors, and endothelial cells. Infusion may be timed to occur at some time after implant which is suitable for the healing of the implant wound to begin. Infusion of angiogenic factors, plasmids encoding for angiogenic factors, and endothelial cells to a region close to sensor electrodes may promote vascular growth near the active enzyme of the sensor. Angiogenic factors, plasmids encoding for angiogenic factors, and endothelial cells may actually be incorporated within an enzyme matrix to promote blood vessel growth into the enzyme region of the sensor. Blood vessel density may be maximized in areas of the placement site structure 110 not covered with a silicone rubber tubing 112. Blood flow rate through any openings in the placement site structure 110 should be sufficient to supply the tissue growing in the interior portion of the placement site structure 110 between the interior walls of the placement site structure 110 and the sensor. Also, the size and spacing between anchor openings in the placement site structure 110 and the sensor opening may be optimized to allow sufficient analyte flux to the sensor. For sensors requiring oxygen, the sensor itself may be designed to overcome oxygen deficit through its own design or by its design in connection with the design of the placement site structure 110.

Embodiments of the present invention may be used in a variety of ways. For example, embodiments of the present invention may be used in connection with THERACYTE, INC. products. THERACYTE, INC., develops and manufactures biocompatible medical device implants that deliver therapies for treatment of chronic and/or deficiency diseases, such as, for example, diabetes. THERACYTE, INC., implants may include biocompatible membranes that induce the development of capillaries close to the membranes, i.e., the implant may be vascularized. Such vascularization promotes a supply of blood to nourish the tissues within the membranes. In addition, the implant may have a thin fluid layer around a sensor placed inside of the implant or infusion site. Current products available from THERACYTE, INC., include 4.5, 20 and 40 microliter size implants. However, embodiments of the present invention can be used in connection with modifications to these products, such as, for example, implants with fewer or greater layers than the implants currently available from THERACYTE, INC.

Embodiments of the present invention may also be used in connection with reusable and non-reusable implant sites or sensor sites. For example, embodiments of the present invention may be used in connection with single or one-time implantations. As another example, embodiments of the present invention may be used in connection with a reusable analyte sensor site for use with a replaceable analyte sensor for determining a level of an analyte includes a site housing. The site housing material may be formed to have an interior cavity with an opening and a conduit that is connected to the opening of the interior tissue ingrowth and vascularization, and yet be free of tissue ingress. Also, the site housing material may permit the analyte to pass through the site housing material to the interior cavity, thus permitting measurement by the replaceable analyte sensor. In addition, the conduit may have a predetermined length to inhibit trauma and encapsulation of tissue occurring at the conduit, which is associated with placing the replaceable analyte sensor in the interior cavity of the site housing, from interfering with the tissue ingrowth and vascularization surrounding the interior cavity of the site housing material. As another example, embodiments of the present invention may be used in connection with a closed vascularized site that includes a thin layer of fluid around the sensor, or a site that has a thin fluid layer on the interior of the site that is used to transmit an analyte to the sensor from the vascularized site in the body. Embodiments of the invention such as those described above are related to U.S. Pat. No. 6,368,274, Reusable Analyte Sensor Site and Method of Using The Same, which is hereby incorporated herein by reference.

Figure 15:
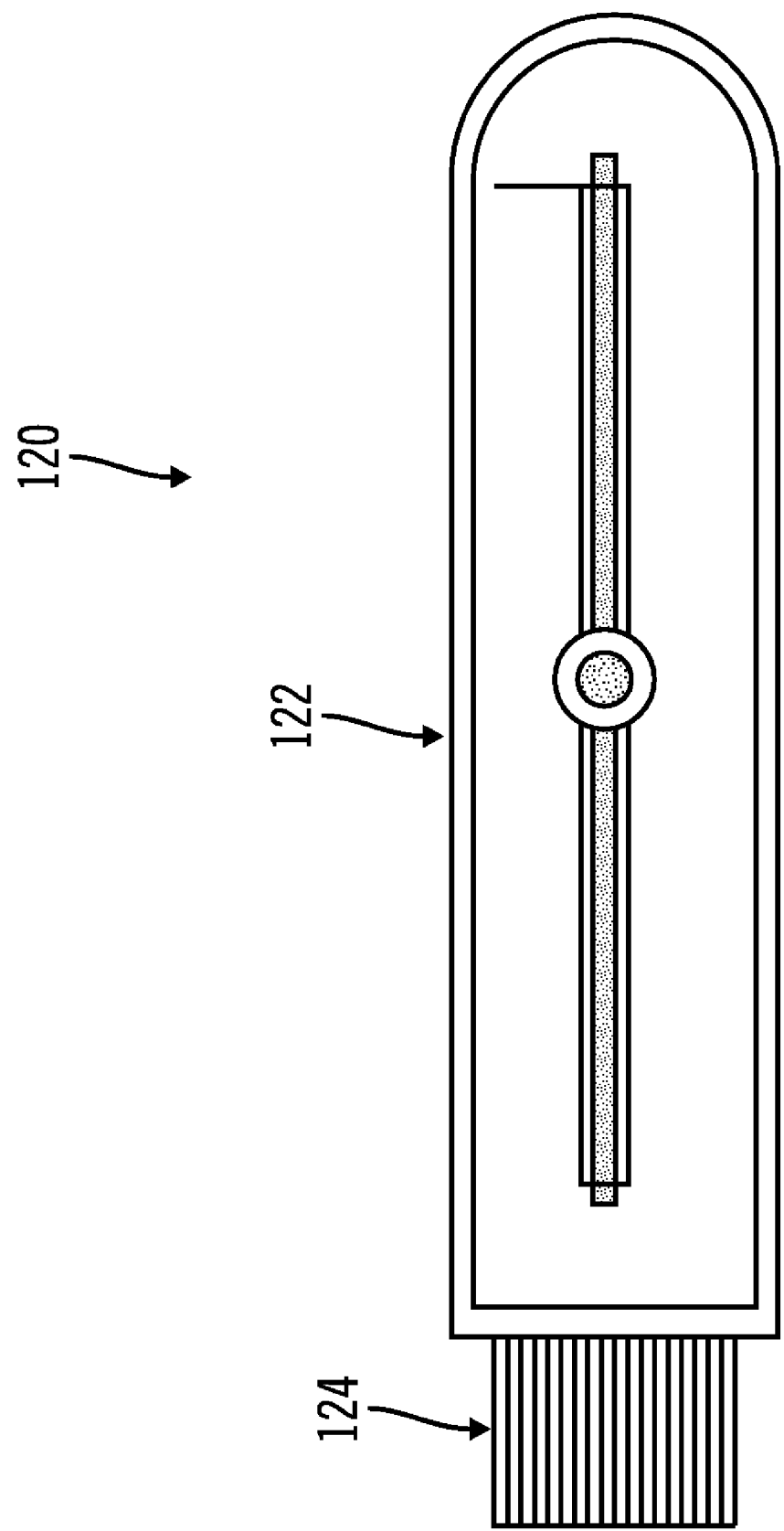
FIG. 15 shows a side cutaway view of a multi-analyte sensing device according to an embodiment of the present invention.
Figure 16:
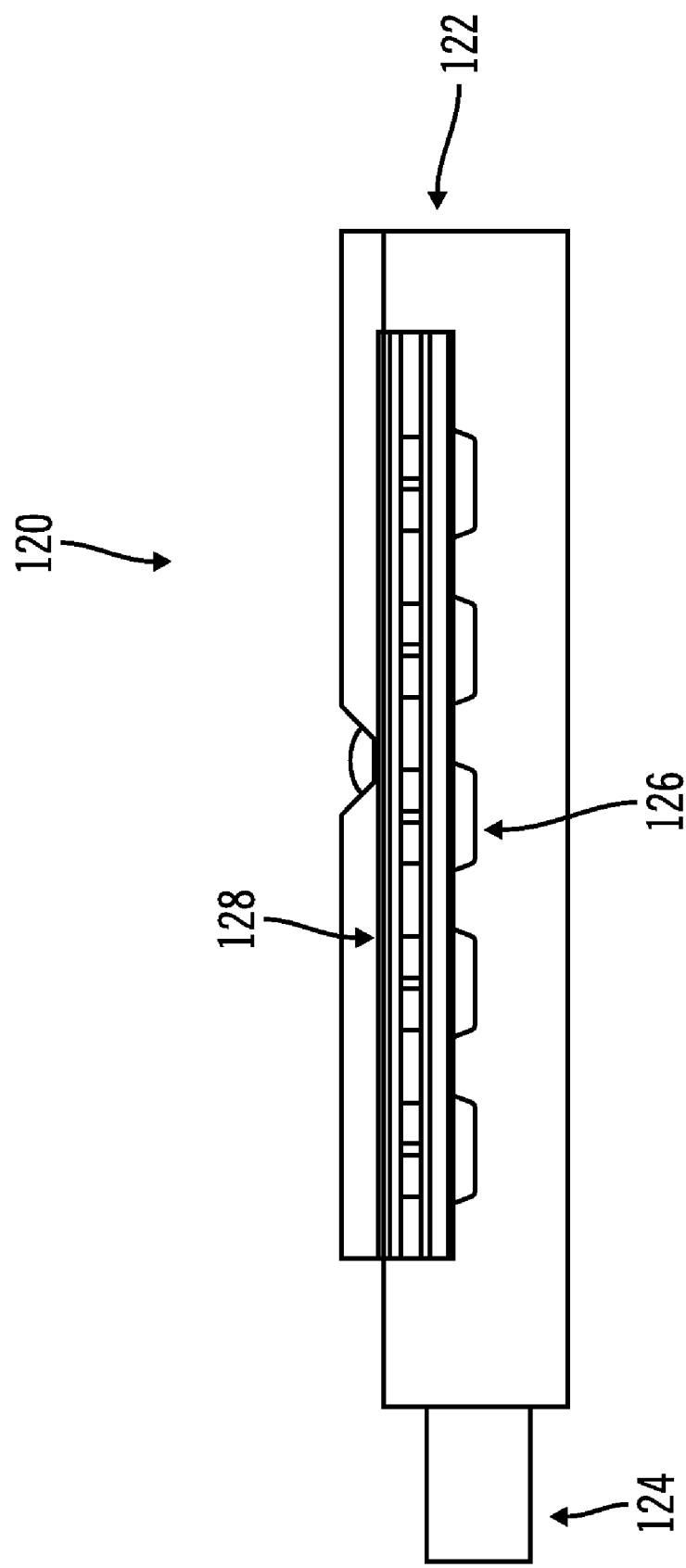
FIG. 16 shows a top view of a multi-analyte sensing device according to an embodiment of the present invention.

A multi-analyte measuring device 120 according to an embodiment of the present invention may be seen in FIGS. 15 and 16. Generally, the multi-analyte measuring device 120 includes, without limitation, a sensor module 122 and a connector 124. The multi-analyte measuring device 120 may be used to measure a variety of analytes for diagnostics, monitoring, evaluation, or other tasks related to physiological or biochemical parameter sensing. The multi-analyte sensing device may be fabricated to be on the order of a few inches, thus making it useful in a variety of places, such as, for example, a hospital, a clinic, an ambulance, a doctor's office, a residence, or even within the body of a patient. Also, depending on the desired application, the multi-analyte measuring device 120 may be fabricated inexpensively enough such that it is disposable.

The multi-analyte measuring device 120 may be self-powered. A power supply such as, for example, a battery or a capacitor, may be used to power the device when positioned in vivo for analyte sensing or measuring. The multi-analyte measuring device 120 may be located in a variety of places in vivo, including, without limitation, in a non-vascular area of the body.

The sensor module 122 may include, without limitation, an integrated circuit 126 and an electrode array 128, as shown in FIG. 16. The electrode array 128 may include electrodes for sensing analytes. The integrated circuit 126 may address, stimulate, measure, and otherwise operate in connection with electrochemical events occurring at the electrode array 128. The sensor module 122 itself may be sized according to its intended application. For example, according to one embodiment of the present invention, a diameter of the sensor module 122 is less than 0.080". According to an embodiment of the present invention, the electrode array 128 may be in direct contact with the integrated circuit 126. According to another embodiment of the present invention, the electrode array 128 may be integral to the integrated circuit 126.

The integrated circuit 126 may be designed to facilitate a variety of applications. For example, according to one embodiment of the present invention, the integrated circuit 126 may be designed such that signals of 1 pA can be detected at a signal-to-noise ration of 100:1. The integrated circuit 126 may also be provided with the capability to make potentiometer, current and coulomb measurements, and may include signal processing, analog-to-digital, and electromagnetic communication circuitry if so desired.

The integrated circuit 126, according to an embodiment of the present invention, may be designed for low current or low charge detection in order to sense low frequency electrochemical events, possibly on the order of sub-ppm quantities for electrochemically active species of for low pulse frequency or low duration sampling of solutions containing concentrated electroactive species on the order of sub-ppm.

According to another embodiment of the present invention, the electrode array 128 environment may be separated from the integrate circuit environment. The separation of the two environments may be facilitated by a three-dimensional structure having an electrical connection between the integrated circuit 126 and the electrode array 128, such as, for example, a multilayer substrate. The structure or device used to separate the two environments may be designed for complete separation or may be designed such that the two environments are permitted to periodically or permanently intermingle, depending on the application.

According to an embodiment of the present invention, the surface of the electrode array 128 may be processed in a manner that imparts specificity to detected events. The surface of the electrode array 128 may include agents to impart specificity to detected events, the agents including, but not limited to, antigens, labeled antigens, antibodies, labeled antibodies, enzymes, membranes, size exclusion membranes, molecularly imprinted membranes, chelating agents, haptens, and other biomolecules such as DNA, for example, and the like. Furthermore, the ability to control electric potential as a function of time via the interaction of the a and an agent on any specific member to the electrode array 128 provides additional capability for enhancing the sensitivity of the multi-analyte measuring device 120.

The substrate on which the electrode array 128 resides may be processed in a manner to create one or more fluidic channels, i.e., gas or liquid channel structures, for example, for the samples containing the analytes. Samples may include, but are not limited to, blood, serum, urine, breath, stool, tissue, and the like. The fluid channel structures may be integral to the substrate containing the electrode array 128 or may be a discrete entity. The properties of the fluid channel structures may depend on the amount of sample delivered to the electrode array 128.

The electrode array 128 may be processed using techniques that are common in the industry, such as, for example, photolithography, screen printing, direct writing and the like. A variety or electrode array 128 properties may be controlled during processing, such as for example, electrode size, spacing, geometry, relative positioning, and the like. Insulators may also be used during processing if desired, and may be used, for example, to tune sensor response. Reference and auxiliary electrodes may be fabricated on the substrate containing the electrode array 128.

Figure 17:
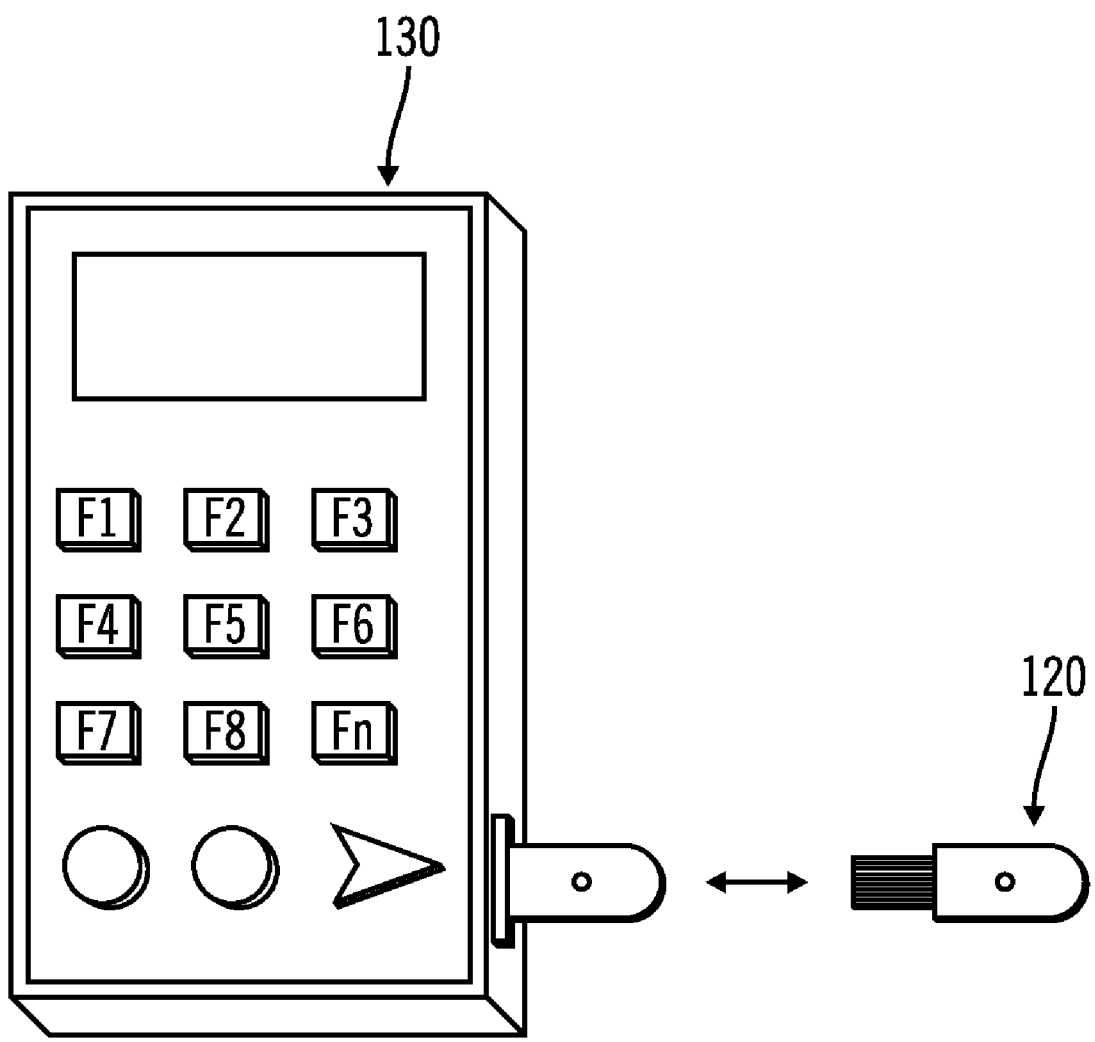
FIG. 17 shows a multi-analyte sensing device and an electronic monitoring/display device according to an embodiment of the present invention.

The multi-analyte measuring device 120 may also include a connector 124 for interfacing to an electronic monitoring device or display 130 as shown in FIG. 17. The connector 124 may provide access to the integrated circuit 126. The connector 124 may be any type of connector commonly used in the art. The electronic monitoring device or display 130 may monitor and/or display a variety of parameters, such as, for example, physiological or biochemical parameters or quantities.

While particular embodiments of the present invention have been shown and described, it will be obvious to those skilled in the art that the invention is not limited to the particular embodiments shown and described and that changes and modifications may be made without departing from the spirit and scope of the appended claims.

What is claimed is:

1. A method for sensing a physiological parameter comprising:
    implanting an implant unit in a non-vascular area of a body;
    allowing a foreign body capsule to form around the implant unit to surround the implant unit;
    providing a sensor lead, a first sensor element on the sensor lead for detecting a physiological parameter, the first sensor element configured to sense a first individual amount of the physiological parameter, and a second sensor element on the sensor lead for detecting the physiological parameter, the second sensor element configured to sense a second individual amount of the physiological parameter, wherein the sensor lead is separate but connectable to the implant unit;
    implanting the sensor lead with the first sensor element and second sensor element in a non-vascular area of the body and connecting the sensor lead to the implant unit;
    sensing the first individual amount and the second individual amount of the physiological parameter and generating a signal representing the first and second individual sensed amounts of the physiological parameter; and
    determining an overall amount of the physiological parameter by calculating a total statistical measurement of the first and second individual sensed amounts from the signals generated from the sensor elements.

2. The method of claim 1, wherein the physiological parameter is at least one of oxygen and glucose.

3. The method of claim 1, wherein the calculating the statistical measurement includes using at least one algorithm that employs values associated with the signal generated from the sensor.

4. The method of claim 1, the method further comprising:
    securing a site housing to the body at a reusable sensor site, the site housing configured for use with the sensor lead.

5. The method of claim 4, the site housing having a cavity for receiving an analyte and a conduit for providing fluid communication between the cavity of the site housing and subcutaneous tissue in the body.

6. The method of claim 5, the site housing comprising a material for allowing the analyte to pass through the material into the cavity of the site housing.

7. The method of claim 5, the conduit having a predetermined length to substantially inhibit trauma to subcutaneous tissue approximately adjacent the conduit.

8. The system of claim 5, the system further comprising:
    a layer of fluid provided on at least a portion of the cavity of the site housing.

9. The method of claim 1, wherein the first sensor element and the second sensor element are comprised in a plurality of spatially separated sensing elements, each of the plurality of spatially separated sensing elements for detecting a sensed amount of a physiological parameter at that spatially separated sensing element and generating a signal representing the sensed amount at that spatially separated sensing element, wherein the sensed amounts from the signals generated from the plurality of spatially separated sensing elements includes the first and second individual sensed amounts; and wherein determining the overall amount of the physiological parameter includes calculating the total statistical measurement of the sensed amounts from the signals generated from the plurality of spatially separated sensing elements.

10. The method of claim 9, the plurality of spatially separated sensing elements being configured in at least one of a one-dimensional array of sensing elements a two-dimensional array of sensing elements, and a three-dimensional array of sensing elements.

11. The method of claim 9, wherein the total statistical measurement is at least one of a maximum amount for the sensed amounts, an average amount of the sensed amounts, a median of the sensed amount, an arithmetic mean of the-sensed amounts, and a weighted arithmetic mean of the sensed amounts.

12. The method of claim 9, wherein the computing element is configured to calculate the total statistical measurement using at least one algorithm that employs values associated with the signals generated from the plurality of spatially separated sensing elements.

13. The method of claim 1, the method further comprising: providing a pump for delivering a drug to the body.

14. The method of claim 13, wherein the providing the pump comprises implanting the pump in the body.

15. The method of claim 1, wherein the non-vascular area of the body includes
subcutaneous tissue.

16. The method of claim 1, wherein the sensor lead is approximately 9 inches long.

17. The method of claim 1, wherein the distance between the first sensing element and the second sensing element is approximately 5 or 6 inches.

18. The method of claim 1, wherein the first sensing element is located near an end of the sensor lead that is connectable to the implant unit and the second sensing element is located near an end of the sensor lead that is furthest away from the end that is connectable to the implant unit.

19. The method of claim 1, wherein the sensor lead and implant unit are both implanted in the peritoneum.

20. The of claim 1, wherein the implant unit includes a pump operable to deliver a drug to the body.

* * * * *